(12) United States Patent
Mathias et al.

(10) Patent No.: US 9,505,709 B2
(45) Date of Patent: Nov. 29, 2016

(54) COMPOSITIONS AND METHODS RELATING TO IONIC SALTS OF PEPTIDES

(71) Applicant: Thetis Pharmaceuticals LLC, Southport, CT (US)

(72) Inventors: Gary Mathias, Ridgefield, CT (US); Banavara L. Mylari, Lutz, FL (US); Frank C. Sciavolino, Waterford, CT (US)

(*) Notice: Subject to any disclaimer, the term of this patent is extended or adjusted under 35 U.S.C. 154(b) by 0 days.

(21) Appl. No.: 14/772,320

(22) PCT Filed: May 4, 2015

(86) PCT No.: PCT/US2015/029091
§ 371 (c)(1),
(2) Date: Sep. 2, 2015

(87) PCT Pub. No.: WO2015/171516
PCT Pub. Date: Nov. 12, 2015

(65) Prior Publication Data
US 2016/0107985 A1    Apr. 21, 2016

Related U.S. Application Data

(60) Provisional application No. 61/988,721, filed on May 5, 2014.

(51) Int. Cl.
| C07C 237/12 | (2006.01) |
| C07C 317/04 | (2006.01) |
| C07C 57/02 | (2006.01) |
| C07D 213/80 | (2006.01) |
| A61K 31/198 | (2006.01) |
| A61K 31/202 | (2006.01) |
| A61P 1/00 | (2006.01) |
| A61P 3/00 | (2006.01) |
| A61P 9/00 | (2006.01) |
| A61P 25/00 | (2006.01) |
| A61P 29/00 | (2006.01) |
| C07K 7/08 | (2006.01) |
| C07C 51/41 | (2006.01) |
| C07C 57/03 | (2006.01) |
| C11C 3/00 | (2006.01) |

(52) U.S. Cl.
CPC ........... *C07C 237/12* (2013.01); *C07C 51/412* (2013.01); *C07C 57/02* (2013.01); *C07C 57/03* (2013.01); *C07C 317/04* (2013.01); *C07D 213/80* (2013.01); *C07K 7/08* (2013.01); *C11C 3/00* (2013.01)

(58) Field of Classification Search
CPC combination set(s) only.
See application file for complete search history.

(56) References Cited

U.S. PATENT DOCUMENTS

| 4,804,539 A | 2/1989 | Guo et al. |
| 4,883,658 A | 11/1989 | Holly |
| 4,914,088 A | 4/1990 | Glonek et al. |
| 5,075,104 A | 12/1991 | Gressel et al. |
| 5,166,320 A | 11/1992 | Wu et al. |
| 5,278,151 A | 1/1994 | Korb et al. |
| 5,294,607 A | 3/1994 | Glonek et al. |
| 5,371,108 A | 12/1994 | Korb et al. |
| 5,578,586 A | 11/1996 | Glonek et al. |
| 5,795,909 A | 8/1998 | Shashoua et al. |
| 6,372,790 B1 | 4/2002 | Bonhomme et al. |
| 6,491,950 B1 | 12/2002 | Gutierrez-Rocca et al. |
| 6,517,870 B1 | 2/2003 | Nishii et al. |
| 6,602,902 B2 | 8/2003 | Shashoua et al. |
| 6,667,064 B2 | 12/2003 | Surette |
| 6,720,001 B2 | 4/2004 | Chen et al. |
| 6,881,854 B2 | 4/2005 | Ptock et al. |
| 6,893,627 B2 | 5/2005 | Ribnicky et al. |
| 7,105,572 B2 | 9/2006 | Sato |
| 7,195,914 B2 | 3/2007 | Surette |
| 7,199,151 B2 | 4/2007 | Shashoua et al. |
| 7,214,387 B2 | 5/2007 | Sanghvi et al. |
| 7,223,770 B2 | 5/2007 | Zhang et al. |
| 7,304,089 B2 | 12/2007 | Kramer et al. |
| 7,429,395 B2 | 9/2008 | Campbell-Tofte |
| 7,553,870 B2 | 6/2009 | Shibuya |
| 7,579,025 B2 | 8/2009 | Campbell-Tofte |
| 7,619,002 B2 | 11/2009 | Shibuya |
| 7,666,898 B2 | 2/2010 | Chang et al. |
| 7,670,612 B2 | 3/2010 | Miller |
| 7,973,073 B2 | 7/2011 | Mylari et al. |
| 8,034,842 B2 | 10/2011 | Bryhn et al. |
| 8,058,312 B2 | 11/2011 | Kim et al. |
| 8,076,377 B2 | 12/2011 | Kim et al. |
| 8,710,041 B2 | 4/2014 | Osterloh et al. |
| 8,765,811 B2 | 7/2014 | Mylari et al. |

(Continued)

FOREIGN PATENT DOCUMENTS

| EP | 2705844 A1 | 3/2014 |
| EP | 2705844 A1 * | 3/2014 |

(Continued)

OTHER PUBLICATIONS

International Search Report mailed on May 8, 2012, for PCT Application No. PCT/US2012/021070, filed Jan. 12, 2012, 3 pages.

(Continued)

*Primary Examiner* — Nyeemah A Grazier
*Assistant Examiner* — Amanda L Aguirre
(74) *Attorney, Agent, or Firm* — Mintz Levin Cohn Ferris Glovsky and Popeo, P.C.; Muriel Liberto, Esq.

(57) ABSTRACT

The present invention relates to compounds of Formula I, compositions containing same, and methods of use.

46 Claims, 8 Drawing Sheets

(56) References Cited

U.S. PATENT DOCUMENTS

| | | |
|---|---|---|
| 8,901,107 B2 | 12/2014 | Mylari et al. |
| 8,906,964 B2 | 12/2014 | Bobotas et al. |
| 8,933,124 B2 | 1/2015 | Mylari et al. |
| 9,012,501 B2 | 4/2015 | Sachetto et al. |
| 9,012,507 B2 | 4/2015 | Mylari et al. |
| 9,216,951 B2 | 12/2015 | Mylari et al. |
| 9,242,008 B2* | 1/2016 | Sciavolino ............ A61K 31/202 |
| 9,382,187 B2 | 7/2016 | Mylari et al. |
| 2003/0077335 A1 | 4/2003 | Richardson et al. |
| 2003/0220301 A1 | 11/2003 | Lal et al. |
| 2004/0191277 A1* | 9/2004 | Sawhney ............. A61K 9/0075 424/400 |
| 2005/0158374 A1 | 7/2005 | Wong et al. |
| 2005/0165102 A1 | 7/2005 | Wong et al. |
| 2005/0182029 A1 | 8/2005 | Lal |
| 2005/0182089 A1 | 8/2005 | Friedl et al. |
| 2006/0084617 A1 | 4/2006 | Satishchandran |
| 2006/0159746 A1 | 7/2006 | Troup et al. |
| 2006/0229359 A1 | 10/2006 | Zhang et al. |
| 2006/0240095 A1 | 10/2006 | Junien et al. |
| 2007/0060532 A1 | 3/2007 | Junien et al. |
| 2007/0207196 A1 | 9/2007 | Zhang |
| 2007/0275019 A9 | 11/2007 | Hakomori et al. |
| 2007/0293449 A1* | 12/2007 | Cui ...................... A61K 9/1272 514/44 A |
| 2007/0293562 A1 | 12/2007 | Mylari et al. |
| 2008/0045559 A1 | 2/2008 | Zhang et al. |
| 2008/0200533 A1 | 8/2008 | Krishnan |
| 2008/0248564 A1 | 10/2008 | Rabbani et al. |
| 2008/0260819 A1 | 10/2008 | Fleming et al. |
| 2009/0047340 A1 | 2/2009 | Guilford |
| 2009/0054513 A1 | 2/2009 | Webster et al. |
| 2009/0156612 A1 | 6/2009 | Kuroita et al. |
| 2009/0227560 A1 | 9/2009 | Kuroita et al. |
| 2010/0035990 A1 | 2/2010 | Bryhn et al. |
| 2010/0105773 A1 | 4/2010 | Smith et al. |
| 2010/0121048 A1 | 5/2010 | Kuroita et al. |
| 2010/0137587 A1 | 6/2010 | Takanobu et al. |
| 2010/0324010 A1 | 12/2010 | Imaeda et al. |
| 2011/0046053 A1 | 2/2011 | Kidron |
| 2011/0052678 A1 | 3/2011 | Shantha et al. |
| 2011/0171142 A1 | 7/2011 | Lara |
| 2012/0178813 A1* | 7/2012 | Mylari .................. A61K 31/202 514/560 |
| 2013/0095140 A1 | 4/2013 | Baron et al. |
| 2013/0281535 A1 | 10/2013 | Mylari et al. |
| 2013/0281536 A1 | 10/2013 | Pinchera et al. |
| 2014/0018419 A1* | 1/2014 | Mylari .................. C07C 279/02 514/482 |
| 2014/0044828 A1 | 2/2014 | Mine et al. |
| 2014/0100273 A1 | 4/2014 | Bobotas et al. |
| 2014/0107360 A1 | 4/2014 | Mylari et al. |
| 2014/0118419 A1 | 5/2014 | Wu et al. |
| 2014/0148464 A1 | 5/2014 | Mylari et al. |
| 2014/0249221 A1 | 9/2014 | Mylari et al. |

FOREIGN PATENT DOCUMENTS

| | | |
|---|---|---|
| WO | WO-02/12177 A1 | 2/2002 |
| WO | WO-03068209 | 8/2003 |
| WO | WO-2003/093449 A2 | 11/2003 |
| WO | WO03093449 A2 * | 11/2003 |
| WO | WO-2004/028469 A2 | 4/2004 |
| WO | WO-2004/082402 | 9/2004 |
| WO | WO-2005041923 A1 | 5/2005 |
| WO | WO-2005042539 A1 | 5/2005 |
| WO | WO-2005118612 A1 | 12/2005 |
| WO | WO-2008/142482 A2 | 11/2008 |
| WO | WO-2008/142482 A3 | 11/2008 |
| WO | WO-2009038396 A2 | 3/2009 |
| WO | WO-2010/12799 A2 | 2/2010 |
| WO | WO-2010127099 A2 | 11/2010 |
| WO | WO-2012/097144 A1 | 7/2012 |
| WO | WO-2013103902 A1 | 7/2013 |
| WO | WO-2014/008379 A2 | 1/2014 |
| WO | WO-2014/008379 A3 | 1/2014 |
| WO | WO-2014/011814 A1 | 1/2014 |
| WO | WO-2014/011895 A2 | 1/2014 |
| WO | WO-2015/171516 A1 | 11/2015 |
| WO | WO-2015/195491 A1 | 12/2015 |

OTHER PUBLICATIONS

Written Opinion mailed on Jul. 22, 2015, for PCT Application No. PCT/US2015/029091, filed May 4, 2015, 5 pages.

"Amino Acid Structures." Web. Nov. 14, 2013. http://www.cem.msu.edu/-cem252/sp97/ch24/ch24aa/html.

"Cold Spring Harbor Protocols." 2006. Web. Nov. 13, 2013. http://cshprotocols.cship.org.

"Eicosapentaenoic Acid pKa." STN Registry File. Web. Nov. 14, 2013.

"Prandimet." RxList. Web. Nov. 14, 2013. http://www.rxlist.com/prandimet-drug.htm.

Charles et al. "Treatment with Metformin of Non-Diabetic Men with Hypertension, Hypertriglyceridaemia and Central Fat Distribution: The BIGPRO 1.2 Trial." *Diabetes Metab. Res. Rev.* 16(2000):2-7.

Goldberg et al. "Lifestyle and Metformin Treatment Favorably Influence Lipoprotein Subfraction Distribution in the Diabetes Prevention Program." *J. Clin. Endocrinol. Metab.* pub. ahead of print Aug. 26, 2013.

Sugiyama et al. "Eicosapentaenoic Acid Lowers Plasma and Liver Cholesterol Levels in the Presence of Peroxisome Profferators-Activate Receptor Alpha." *Life Sciences.* 83(2008):19-28.

Wulffele et al. "The Effect of Metformin on Blood Pressure, Plasma Cholesterol and Triglycerides in Type 2 Diabetes Mellitus: A Systematic Review." *J. Intern. Med.* 256.1(2004):1-14.

International Search Report issued in PCT/US2013/049984 on Nov. 28, 2013.

International Search Report issued in PCT/US2015/029091 on Jul. 14, 2015 (9 Pages).

* cited by examiner

TP-312-1 Hyperemia

TP-312-1 Squinting

TP-312-1 Discharge

COMPOSITIONS AND METHODS RELATING TO IONIC SALTS OF PEPTIDES

RELATED APPLICATION

This application is a national stage application, filed under 35 U.S.C. §371, of international Application No. PCT/US2015/029091 filed on May 4, 2015, which claims priority to U.S. Provisional Application No. 61/988,721 filed on May 5, 2014, the contents of which are hereby fully incorporated by reference.

FIELD OF THE INVENTION

The present invention relates to the field of drug delivery and particularly the use of peptide-comprising ionic salt compounds and compositions containing same for delivery of nutraceutical or therapeutic agents to a subject.

BACKGROUND OF THE INVENTION

U.S. 20140044828 describes nutritional compositions containing specified amounts of n-3 fatty acids and one or more of free lysine, dipeptides containing lysine, and lysine salts, for the prophylaxis and/or treatment of various symptoms associated with muscle mass decrease, decreased basal metabolism, and low body temperature, as well as for suppression of obesity, suppression of visceral fat accumulation, and treatment of hyperglycemia and hyperlipidemia, particularly in the elderly. The term "dipeptides containing lysine" is defined as referring to a dipeptide where at least one molecule of the dipeptide is lysine or a salt of lysine such as L-lysine hydrochloride, L-lysine acetate, and L-lysine glutamate. Lysyllysine is given as a specific example of a dipeptide containing lysine.

Lysyllysine is described in U.S. 20080248564 in a process for the covalent modification of nucleic acids by lactosylation for more efficient transfer of nucleic acids into cells. This is described as an improvement over prior art methods relying on the formation of non-specific ionic complexes between nucleic acids and polycations such as polylysine, as described in U.S. Pat. No. 5,166,320. U.S. 20060084617 describes the use of lysyllysine in a process for conjugating endosomolytic spermine to nucleic acids to enhance their delivery into cells.

U.S. 20070275019 describes the preparation of vaccines directed to cancer-associated carbohydrate antigens, the vaccines comprising multivalent antigen systems in which lysyllysine is used as a core matrix bearing multiple antigens as dendritic arms Polyunsaturated fatty acids of the omega-3 series ("omega-3 fatty acids") have shown a wide spectrum of biological activities suggesting their possible usefulness in treating a range of diseases and disorders including metabolic disorders, cardiovascular complications, inflammatory diseases, central nervous system disorders, and ophthalmic complications. But the poor aqueous solubility of omega-3 fatty acids limits their utility as therapeutic agents and as nutraceutical additives to food and drink due to a phenomenon referred to as solubility-limited absorption which limits the plasma levels that can be achieved following oral administration. In fact, the omega-3 fatty acids are essentially insoluble in water and both the free acid and sodium salt forms create soap-like emulsions when mixed with water. Thus, although omega-3 fatty acids are absorbed following oral administration, the relatively low plasma levels achieved cannot be increased simply by increasing the dose administered.

WO 2014/011895 describes fatty acid salts of eicosapentaenoic acid (EPA) with lysine or docosahexaenoic acid (DHA) or EPA with metformin, piperazine, and meglumine. The compositions provide for increased aqueous solubility of the fatty acid.

In addition to their poor aqueous solubility, omega-3 fatty acids suffer from susceptibility to lipid oxidation. This oxidation leads to formation of undesirable fishy and rancid off-flavors that render compositions comprising them less palatable.

There is a need to develop compositions able to deliver omega-3 fatty acids at much higher plasma levels than is possible using the currently available free fatty acid, sodium salt, or ester forms, in order to fulfill the therapeutic promise of these compounds and translate the many promising in vitro and cellular pharmacology observations into clinical benefits. Such compositions should demonstrate increased aqueous solubility of omeg-3 fatty acids which would facilitate their use in both oral dosage forms, ophthalmic drops, and intravenous dosage forms. There is also a need to develop compositions that provide improved stability of the omega-3 fatty acids against lipid oxidation. The present invention addresses these needs.

SUMMARY OF THE INVENTION

The present invention provides compounds of Formula I or an enantiomer, polymorph, solvate, or hydrate thereof:

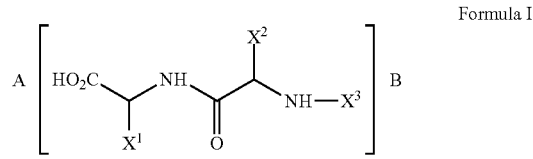

Formula I wherein

A and B are each a molecule having at least one acidic function,

A and B may be the same or different, either A or B, but not both, may be absent, $X_1$ and $X_2$ each refer to a branched or unbranched carbon chain of from 1 to 10 carbons comprising at least one basic function, and $X_3$ is H or CO—Z and Z is a peptide of from 1 to 20 amino acids, or a pharmaceutically acceptable salt thereof.

The basic function may be selected from a primary amine, a secondary amine, a tertiary amine, and a guanidine.

In one embodiment, $X_1$ and $X_2$ are independently selected from $(CH_2)_3$—$R_1$, and $(CH_2)_4$—$R_2$, where $R_1$ and $R_2$ are each a basic function which may be the same or different. In one embodiment, $X_3$ is H. In one embodiment, $X_1$ and $X_2$ are both $(CH_2)_4$—$R_2$, $R_2$ is $NH_3+$, and $X_3$ is H. In one embodiment, $X_1$ and $X_2$ are both $(CH_2)_3$—$R_1$, $R_1$ is $NHC(NH_2+)NH_2$, and $X_3$ is H. In one embodiment, $X_1$ is $(CH_2)_3$—$R_1$, $R_1$ is $NHC(NH_2+)NH_2$, $X_2$ is $(CH_2)_4$—$R_2$, $R_2$ is $NH_3+$, and $X_3$ is H. In one embodiment, $X_1$ is $(CH_2)_4$—$R_2$, $R_2$ is $NH_3+$, $X_2$ is $(CH_2)_3$—$R_1$, $R_1$ is $NHC(NH_2+)NH_2$, and $X_3$ is H.

In one embodiment, A or B, or both, is a polyunsaturated fatty acid. In one embodiment, the polyunsaturated fatty acid is an omega-3 fatty acid selected from the group consisting of eicosapentaenoic acid (EPA), docosahexaenoic acid (DHA), docosapentaenoic acid (DPA), hexadecatrienoic acid (HTA), α-linolenic acid (ALA), stearidonic acid (SDA), eicosatrienoic acid (ETE), eicosatetraenoic acid (ETA), heneicosapentaenoic acid (HPA), tetracosapentaenoic acid, and tetracosahexaenoic acid. In one embodiment, the polyunsaturated fatty acid is an omega-6 fatty acid selected from the group consisting of linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (Osbond acid), tetracosatetraenoic acid, and tetracosapentaenoic acid, 24:5 (n-6). In one embodiment, the polyunsaturated fatty acid is an omega-9 fatty acid selected from the group consisting of mead acid, 20:3 (n-9), all-cis-5,8,11-eicosatrienoic acid, oleic acid, eicosenoic acid, erucic acid, and nervonic acid.

In one embodiment, A or B, or both, are a non-fatty acid molecule selected from the group consisting of methanesulfonic acid, niacin, difluoromethylornithine, lipoic acid, gabapentin, pre-gabalin, indomethacin, sulindac, ibuprofen, naproxen, salicylic acid, acetylsalicylic acid, salicylsalicylic, and meloxicam.

The invention also provides compositions comprising a compound of Formula I. In one embodiment, the composition is a pharmaceutical or nutriceutical composition and the carrier is acceptable for administration to humans or animals. In one embodiment, the composition is a nutriceutical additive or supplement. In one embodiment, the invention provides a food or drink product comprising a nutriceutical additive of the invention. In one embodiment, the composition is a pharmaceutical composition in the form of a solid oral dosage form, an intravenous dosage form, or an ophthalmic formulation.

In one embodiment, the pharmaceutical composition comprises a compound of Formula I wherein A or B, or both, are a polyunsaturated fatty acid. In one embodiment, the polyunsaturated fatty acid is an omega-3 fatty acid independently selected from eicosapentaenoic acid (EPA), docosahexaenoic acid (DHA), and docosapentaenoic acid (DPA). The invention also provides methods of use for such pharmaceutical compositions. In one embodiment, the pharmaceutical composition is used in a method for lowering serum triglycerides in a subject, preferably a human subject. In one embodiment, the pharmaceutical composition is administered to a subject in need thereof in an amount effective to lower elevated serum triglycerides in a human subject by at least 0.5 mmol/L, preferably at least 1 mmol/L. In one embodiment, the subject is a human subject having severe hypertriglyceridemia characterized by serum triglyceride levels of from 500 to 2,000 mg/dl. In one embodiment, the pharmaceutical composition is used in a method for treating a metabolic disease or disorder in a subject, preferably a human subject, the disease or disorder selected from the group consisting of hypertriglyceridemia, severe hypertriglyceridemia, hypercholesterolemia, pre-diabetes, fatty liver disease, and obesity. In one embodiment, the pharmaceutical composition is used in a method for treating a cardiovascular disease or disorder selected from atrial fibrillation, myocardial infarction, and congestive heart failure. In one embodiment, the pharmaceutical composition is used in a method for treating an inflammatory disease or disorder selected from arthritis, irritable bowel syndrome, ophthalmic inflammation disorders, and dry eye syndrome. In one embodiment, the pharmaceutical composition is used in a method for treating a gastrointestinal disorder or complication thereof selected from bowel obstruction, short bowel syndrome, Gastroschisis, prolonged diarrhea regardless of its cause, high-output fistula, very severe Crohn's disease, ulcerative colitis, colon cancer or familial adenomatous polyposis, parenteral nutrition-associated liver disease, essential fatty acid deficiency or other pediatric GI disorders including congenital GI anomalies and necrotizing enterocolitis. In one embodiment, the pharmaceutical composition is used in a method for treating a neurological disorder selected from Alzheimer's disease, attention deficit hyperactivity disorder (ADHD), depression, traumatic brain injury, spinal cord injury, ischemic stroke, and concussion.

In one embodiment, the pharmaceutical composition comprises a compound of Formula I wherein A or B, or both, is selected from gabapentin and a non-steroidal anti-inflammatory agent (NSAID), wherein, if only one of A or B is gabapentin or a non-steroidal anti-inflammatory agent (NSAID), the other is a polyunsaturated fatty acid, preferably selected from EPA, DHA, or DPA. The invention also provides methods of use for such pharmaceutical compositions. In one embodiment, both A and B are gabapentin and the pharmaceutical composition is used in a method for treating epilepsy or epileptic syndrome. In one embodiment, one of A or B is gabapentin and the other is a polyunsaturated fatty acid, preferably selected from EPA, DHA, or DPA and the pharmaceutical composition is used in a method for treating nociceptive pain. In one embodiment, one of A or B is a NSAID and the other is a polyunsaturated fatty acid, preferably selected from EPA, DHA, or DPA and the pharmaceutical composition is used in a method for treating neuropathic pain.

The invention also provides a package or kit comprising a unit dosage form of a composition of the invention, at least one container for holding the unit dosage forms, and instructions for use.

The invention also provides a method of achieving an initial (from time 0.5 to 2 hrs post-administration) free fatty acid plasma concentration of an omega-3 fatty acid in a subject that is from 2 to 5 times higher than the initial free fatty acid plasma concentration achievable from administering the free fatty acid form of the omega-3 fatty acid, the method comprising administering to the subject by an oral or intravenous route an amount of a pharmaceutical composition comprising a compound of Formula I wherein A or B, or both, are a omega-3 fatty acid.

DETAILED DESCRIPTION OF THE INVENTION

Figure 1:
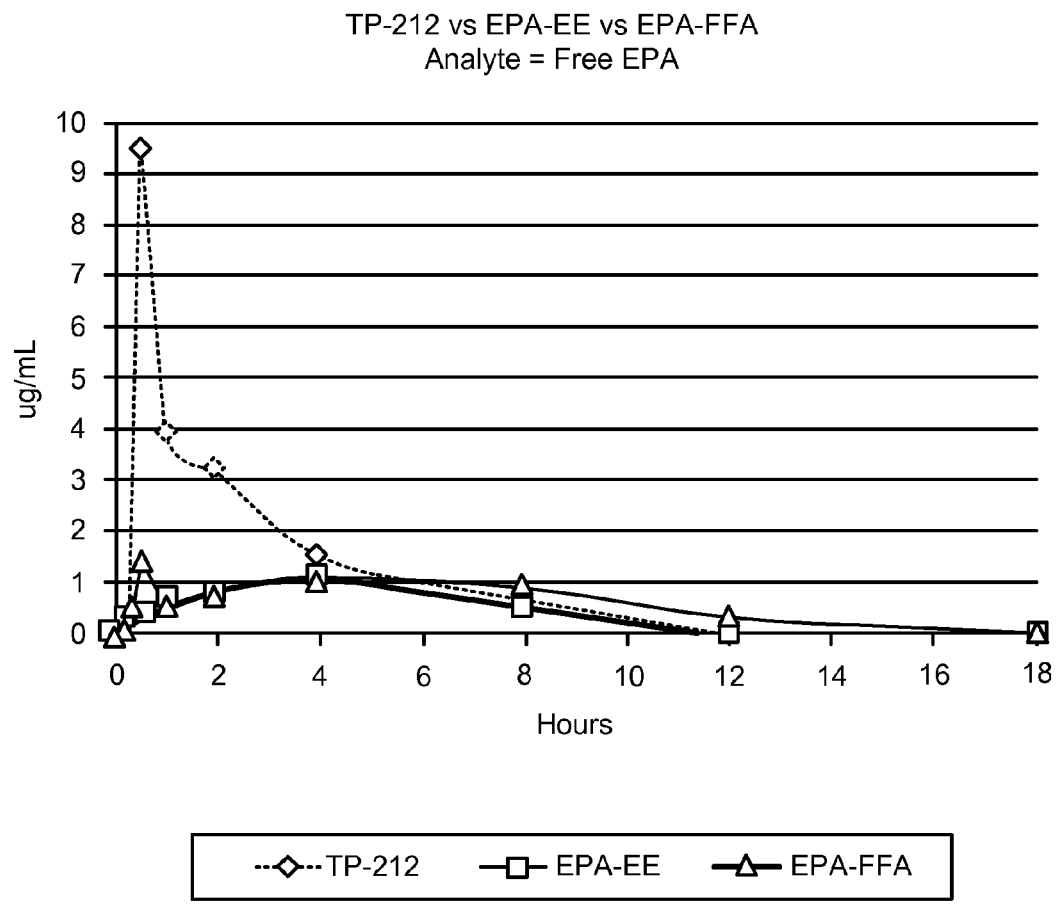
FIG. 1: plasma levels of free EPA of TP-212 compared to EPA-EE and EPA-FFA, all administered via oral gavage.

The invention relates to ionic salt compounds in which the cation is contributed by a peptide component consisting of at least two amino acid moieties each having at least one basic function, and the counter-ion is contributed by a counter-ion component consisting of one or two molecules, each having at least one acidic function. Each molecule of the counter-ion component is coordinated around the at least one basic function of each amino acid moiety of the peptide component.

Each amino acid moiety of the peptide component may, independently, comprise or consist of a single natural or non-naturally occurring amino acid, or a peptide of from 2 to 5 natural or non-naturally occurring amino acids, or combinations thereof. In all cases, each amino moiety is either a single amino acid or a branched or unbranched carbon chain of from 2 to 5 carbons comprising at least one basic function. In one embodiment, the at least one basic function is selected from the group consisting of a primary amine, a secondary amine, a tertiary amine, and a guanidine. In one embodiment, the basic function is a primary amine. In one embodiment, the primary amine is the terminal amine of an amino acid side chain, wherein the amino acid is a natural or non-naturally occurring amino acid. In one embodiment, the amino acid is a naturally occurring amino acid selected from arginine and lysine. In one embodiment, the peptide component consists of two amino acid moieties. In one embodiment, the two amino acid moieties are independently selected from lysine, arginine, and derivatives thereof. Preferably, the counterion molecule is a therapeutic agent. In one aspect, the therapeutic agent is poorly water soluble and/or chemically unstable, e.g., due to its susceptibility to oxidative or other degradation. In one embodiment, the counterion molecule is selected from an omega-3 fatty acid and a non-omega-3 fatty acid therapeutic agent. In one embodiment, the compound has both an omega-3 fatty acid and a non-omega-3 fatty acid counterion molecule. The invention also provides compositions comprising same, and methods of making and using the compositions.

The present invention provides compounds of Formula I, including enantiomers, polymorphs, solvates, and hydrates thereof:

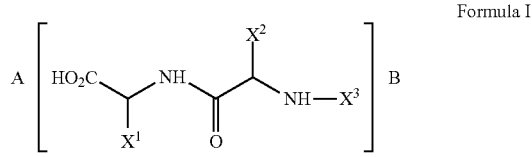

Formula I wherein
A and B are each a molecule having at least one acidic function,
A and B may be the same or different,
either A or B, but not both, may be absent,
$X_1$ and $X_2$ each refer to a branched or unbranched carbon chain of from 1 to 10 carbons comprising at least one basic function, and
$X_3$ is H or CO—Z and Z is a peptide of from 1 to 20 amino acids, or a pharmaceutically acceptable salt thereof.

In one embodiment, $X_1$ and $X_2$ are independently selected from $(CH_2)_3$—$R_1$, and $(CH_2)_4$—$R_2$, where $R_1$ and $R_2$ are each a basic function which may be the same or different. In one embodiment, the basic function is selected from a primary amine, a secondary amine, a tertiary amine, and a guanidine. In one embodiment, $R_1$ is $NHC(NH_2+)NH_2$. In one embodiment $R_2$ is $NH_3+$.

In one embodiment, $X_1$ and $X_2$ are the same and are each $(CH_2)_3$—$R_1$ and $R_1$ is $NHC(NH_2+)NH_2$. In one embodiment, $X_1$ and $X_2$ are the same and are each $(CH_2)_4$—$R_2$ and $R_2$ is $NH_3+$.

In one embodiment, $X_1$ and $X_2$ are different. In one embodiment, $X_1$ is $(CH_2)_3$—$R_1$, $R_1$ is $NHC(NH_2+)NH_2$, $X_2$ is $(CH_2)_4$—$R_2$ and $R_2$ is $NH_3+$. In one embodiment, $X_1$ is $(CH_2)_4$—$R_2$, $R_2$ is $NH_3+$, $X_2$ is $(CH_2)_3$—$R_1$, and $R_1$ is $NHC(NH_2+)NH_2$.

In one embodiment, $X_3$ is H. In one embodiment, $X_3$ is H, $X_1$ is $(CH_2)_3$—$R_1$, and $X_2$ is $(CH_2)_4$—$R_2$, where $R_1$ and $R_2$ are each $NHC(NH_2+)NH_2$ and $NH_3+$, respectively. In one embodiment, $X_3$ is H, $X_1$ is $(CH_2)_4$—$R_1$, $X_2$ is $(CH_2)_3$—$R_2$, where $R_1$ and $R_2$ are each $NH_3+$ and $NHC(NH_2+)NH_2$, respectively. In one embodiment, $X_3$ is H, $X_1$ and $X_2$ are the same and are each $(CH_2)_4$—$R_2$ and $R_2$ is $NH_3+$. In one embodiment, $X_3$ is H, $X_1$ and $X_2$ are the same and are each $(CH_2)_3$—$R_1$ and $R_1$ is $NHC(NH_2+)NH_2$.

In one embodiment, $X_3$ is CO—Z and Z is a peptide of from 1 to 20 amino acids. In one embodiment, the peptide is a peptide of from 1 to 10 or from 1 to 5 amino acids. The amino acids may be any natural or non-naturally occurring amino acids. In one embodiment, the amino acids are independently selected from glycine, alanine, valine, leucine, isoleucine, serine, cysteine, threonine, methionine, proline, phenylalanine, tyrosine, tryptophan, histidine, lysine, arginine, aspartic acid, glutamic acid, asparagine, and glutamine, or salts thereof. The amino salts may be, for example, the hydrochloride, citrate, tartarate, monohydrogen-, dihydrogen-, and trihydrogen phosphate, methanesulfonate, benzenesulfonate and borate salt.

In one embodiment, either A or B is absent. Where either A or B is absent, the compound may be referred to as "mono" salt. In one embodiment, A and B are both present. Where A and B are both present, the compound may be referred to as a "bis" salt.

In one embodiment, A and B are each a fatty acid and A and B are the same or different. In another embodiment, A or B is a fatty acid and the other molecule of the counter-ion component is a non-fatty acid molecule. In one embodiment, both A and B are a non-fatty acid molecule. In one embodiment, the molecule is selected from methanesulfonic acid, niacin, difluoromethylornithine (also referred to as eflornithine), including its optical forms (e.g., D, L and racemic mixtures), lipoic acid, including its optical forms (e.g., D, L and racemic mixtures), gabapentin, pre-gabalin, indomethacin, sulindac, ibuprofen, naproxen, salicylic acid, acetylsalicylic acid, salicylsalicylic, and meloxicam. In one embodiment, the molecule is selected from salicylic acid, acetylsalicylic acid, and salicylsalicylic. In one embodiment, the non-fatty acid molecule is a therapeutic agent.

The term "fatty acid" is used to describe a carboxylic acid with a long aliphatic carbon chain for from about 4 to 28 carbon atoms, which is either saturated or unsaturated, referring to whether the carbon chain contains one or more double bonds between the carbon atoms (unsaturated). In one embodiment, the fatty acid is an unsaturated fatty acid. In one embodiment, the unsaturated fatty acid is a mono-, di-, or polyunsaturated fatty acid. In one embodiment, the fatty acid is a polyunsaturated fatty acid. In one embodiment, the polyunsaturated fatty acid is a long-chain polyunsaturated fatty acid having 16 to 24 carbon atoms ($C_{16}$-$C_{24}$), or 20 to 22 carbon atoms ($C_{20}$-$C_{22}$). In one embodiment, the polyunsaturated fatty acid is a fatty acid of the omega-3, omega-6, omega-7, or omega-9 series. In one embodiment, the fatty acid is selected from a mono-, di-, or polyunsaturated fatty acid of the omega-3, omega-6, omega-7, or omega-9 series. Examples of fatty acids of the omega-3, 6, 7, and 9 series are provided in Table 1 below. In one embodiment, the fatty acid is selected from a fatty acid set forth in Table 1.

In one embodiment, the omega-3 fatty acid is selected from the group consisting of hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA, clupanodonic acid), docosahexaenoic acid (DHA, Cervonic acid), tetracosapentaenoic acid, 24:5 (n-3), and tetracosahexaenoic acid (Nisinic acid), 24:6 (n-3).

TABLE 1

Fatty acids (mono- and di-unsaturated) of the omega-3, 6, 7, and 9 series.

| Common name | Lipid name | Chemical name |
|---|---|---|
| Hexadecatrienoic acid (HTA) | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (SDA) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |
| Linoleic acid (LA) | 18:2 (n-6) | all-cis-9,12-octadecadienoic acid |
| Gamma-linolenic acid (GLA) | 18:3 (n-6) | all-cis-6,9,12-octadecatrienoic acid |
| Calendic acid | 18:3 (n-6) | 8E,10E,12Z-octadecatrienoic acid |
| Eicosadienoic acid | 20:2 (n-6) | all-cis-11,14-eicosadienoic acid |
| Dihomo-gamma-linolenic acid (DGLA) | 20:3 (n-6) | all-cis-8,11,14-eicosatrienoic acid |
| Arachidonic acid (AA) | 20:4 (n-6) | all-cis-5,8,11,14-eicosatetraenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid | 22:5 (n-6) | all-cis-4,7,10,13,16-docosapentaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |
| none | 12:1 (n-7) | 5-Dodecenoic acid |
| none | 14:1 (n-7) | 7-Tetradecenoic acid |
| Palmitoleic acid | 16:1 (n-7) | 9-Hexadecenoic acid |
| Vaccenic acid | 18:1 (n-7) | 11-Octadecenoic acid |
| Paullinic acid | 20:1 (n-7) | 13-Eicosenoic acid |
| none | 22:1 (n-7) | 15-Docosenoic acid |
| none | 24:1 (n-7) | 17-Tetracosenoic acid |
| oleic acid | 18:1 (n-9) | 9-octadecenoic acid |
| elaidic acid | 18:1 (n-9) | (E)-octadec-9-enoic acid |
| gondoic acid | 20:1 (n-9) | 11-eicosenoic acid |
| mead acid | 20:3 (n-9) | 5,8,11-eicosatrienoic acid |
| erucic acid | 22:1 (n-9) | 13-docosenoic acid |
| nervonic acid | 24:1 (n-9) | 15-tetracosenoic acid |
| Conjugated Linoleic Acids (two conjugated double bonds) | | |
| Rumenic acid | 18:2 (n-7) | 9Z,11E-octadeca-9,11-dienoic acid |
|  | 18:2 (n-6) | 10E,12Z-octadeca-9,11-dienoic acid |
| Conjugated Linolenic Acids (three conjugated double bonds) | | |
| α-Calendic acid | 18:3 (n-6) | 8E,10E,12Z-octadecatrienoic acid |
| β-Calendic acid | 18:3 (n-6) | 8E,10E,12E-octadecatrienoic acid |
| Jacaric acid | 18:3 (n-6) | 8Z,10E,12Z-octadecatrienoic acid |
| α-Eleostearic acid | 18:3 (n-5) | 9Z,11E,13E-octadeca-9,11,13-trienoic acid |
| β-Eleostearic acid | 18:3 (n-5) | 9E,11E,13E-octadeca-9,11,13-trienoic acid |
| Catalpic acid | 18:3 (n-5) | 9Z,11Z,13E-octadeca-9,11,13-trienoic acid |
| Punicic acid | 18:3 (n-5) | 9Z,11E,13Z-octadeca-9,11,13-trienoic acid |
| Other | | |
| Rumelenic acid | 18:3 (n-3) | 9E,11Z,15-octadeca-9,11,15-trienoic acid |
| α-Parinaric acid | 18:4 (n-3) | 9E,11Z,13Z,15E-octadeca-9,11,13,15-tetraenoic acid |
| β-Parinaric acid | 18:4 (n-3) | all trans-octadeca-9,11,13,15-tretraenoic acid |
| Bosseopentaenoic acid | 20:5 (n-6) | 5Z,8Z,10E,12E,14Z-eicosanoic acid |
| Pinolenic acid | 18:3 (n-6) | (5Z,9Z,12Z)-octadeca-5,9,12-trienoic acid |
| Podocarpic acid | 20:3 (n-6) | (5Z,11Z,14Z)-eicosa-5,11,14-trienoic acid |

In one embodiment, the omega-3 fatty acid is selected from eicosapentaenoic acid (EPA), docosahexaenoic acid (DHA), and docosapentaenoic acid (DPA). In one embodiment, the omega-3 fatty acids are independently selected from EPA, DHA, DPA, hexadecatrienoic acid (HTA), α-linolenic acid (ALA), stearidonic acid (SDA), eicosatrienoic acid (ETE), eicosatetraenoic acid (ETA), heneicosapentaenoic acid (HPA), tetracosapentaenoic acid, and tetracosahexaenoic acid. In one embodiment, the counter-ion component comprises two omega-3 fatty acids that are the same.

In accordance with any of the embodiments described herein, the omega-6 fatty acids may be selected from the group consisting of linoleic acid, gamma-linolenic acid (GLA), eicosadienoic acid, dihomo-gamma-linolenic acid (DGLA), arachidonic acid (AA), docosadienoic acid, adrenic acid, docosapentaenoic acid (Osbond acid), tetracosatetraenoic acid, and tetracosapentaenoic acid, 24:5 (n-6).

In accordance with any of the embodiments described herein, the omega-9 fatty acids may be selected from the group consisting of mead acid, 20:3 (n-9), all-cis-5,8,11-eicosatrienoic acid, oleic acid, eicosenoic acid, erucic acid, and nervonic acid.

In one embodiment, the omega-3 fatty acid component of the ionic salt is independently selected from eicosapentaenoic acid (EPA), docosahexaenoic acid (DHA), and docosapentaenoic acid (DPA).

In one embodiment, the invention provides a compound of Formula I selected from the group consisting of Lysyl-lysine EPA, Lysyl-lysine bis-EPA, Lysyl-lysine DHA, Lysyl-lysine bis DHA, Lysyl-lysine EPA DHA, Lysyl-lysine bis gabapentin, Lysyl-lysine EPA niacin, lysyl-lysine EPA ibuprofen, lysyl-lysine EPA methanesulfonic acid salt, arginyl-lysine bis gabapentin, and arginyl-arginine bis gabapentin.

In certain embodiments, the invention provides a solvate of a compound of Formula I described herein. A "solvate" refers to a form of salt bound by a non-covalent bond to another molecule (such as a polar solvent). Such solvates are typically crystalline solids having a substantially fixed molar ratio of solute and solvent. When the solvent is water, the solvate formed is a hydrate. Example hydrates include hemihydrates, mono hydrates, dihydrates, etc.

In one embodiment, the invention provides a crystalline form of a compound of Formula I described herein. In one embodiment, the invention provides a polymorph of an ionic salt described herein.

Physical Properties

The compounds of Formula I and the compositions of the invention possess superior chemical and physical stability, for example as compared to mixtures of free fatty acids or the ethyl ester or glyceryl ester forms of the fatty acids. Physically, the compounds and compositions of the invention are solid, free flowing substances suitable for formulation into solid dosage forms such as powders, tablets, capsules or caplets. In addition, the compounds and compositions of the invention can be readily combined, e.g., by physical admixture, with other biologically active agents in a solid dosage form. As such, the compounds and compositions described here are different from, and advantageous over, other fatty acid compositions known in the art, which are generally in the physical form of an oily liquid.

Thus, the compounds and compositions of the invention provide a physically and chemically stable form of fatty acids useful, for example, in the formulation of solid dosage forms of fatty acids for human and animal consumption. The fatty acid component of the compounds and compositions of the invention possesses superior chemical and physical stability compared to the free fatty acid or ester forms of the fatty acids, e.g., the ethyl ester, or glyceryl ester forms of the fatty acids. This stability stems, in part, from the solid state, free-flowing nature of the compounds and compositions described herein, which are chemically and physically more stable than the liquid oil form of the free fatty acids and esters. For example, the fatty acid component of the solid compounds and compositions described here is relatively stable against chemical degradation, such as oxidative degradation, to which the fatty acid oils are highly susceptible. In particular, the compositions described here are advantageously stable to air, oxygen, and humidity such that no change in physical properties, such as flow characteristics, or in chemical properties, as measured by NMR spectroscopy, occur following days of storage in an open vial at room temperature and standard humidity.

The compositions of the invention advantageously provide unexpectedly high bioavailability of the fatty acid component due to the tendency of the counter-ion component to completely dissociate in aqueous media within the pH range of 8.0 to below 1.0, and well within the pH range commonly observed in the stomach and upper GI tract of most humans and non-human animal species.

In one embodiment, the compositions of the invention are able to deliver at least twice as much free fatty acid in serum during the initial 2 hours following oral or intravenous administration. Accordingly, the invention also provides methods for achieving increased bioavailability of free omega-3 fatty acids following oral or intravenous administration of a composition of the invention.

The compounds and compositions of the invention also provide improved bioavailability of the fatty acid component as compared to, for example, free fatty acids and esters of the fatty acids. The pharmacokinetic properties of the compounds and compositions of the invention relate, in part, to their advantageous property of completely dissociating into their component ionic species upon immersion in aqueous media from alkaline to acidic pH, including gastric or gastrointestinal fluid. Thus, when a composition (or compound) of the invention is immersed in aqueous media, the counter-ion component (i.e., the fatty acid) of Formula I dissociates into its ionic form, i.e., ionic forms of the free fatty acids. The compounds and compositions of the invention are therefore useful for delivering fatty acids, and in particular free fatty acids in their ionic form, to a human or animal subject.

The solid, free-flowing character of the compounds of the invention also provides for ease of their formulation in physical admixture with other biologically active agents in a solid dosage form. In one embodiment, the solid dosage form is adapted for oral delivery. The solid dosage form may also be adapted for other routes of administration, as described infra.

The compounds of the invention may provide for increased water solubility and/or stability of a molecule of the counter-ion component compared to the molecule itself In one embodiment, the compounds of the invention allow for the systemic delivery of higher amounts of a poorly water soluble molecule in the counter-ion component, when administered to a subject, for example by an oral or intravenous route, as compared to the molecule itself In some embodiments, molecule of the counter-ion component also has increased bioavailability when administered by an oral or intravenous route, as compared to the molecule itself In one embodiment, a compound of Formula I having one or two polyunsaturated fatty acid molecules as the counterion component provides for relatively high aqueous solubility of the fatty acid molecule compared to, for example, the aqueous solubility of the free fatty acid or ester form of the fatty acid, including e.g., ethyl esters and glycerol esters, such as triglycerol ester, phosphatidyl choline, etc. In one embodiment, the compound is soluble in water in a range of from about 10 to 100 mg/ml. A compound having a single fatty acid component A or B (also referred to herein as a "mono" salt, as opposed to a compound having both A and B fatty acid components, referred to herein as a "bis" salt) may have an aqueous solubility in the range of, for example, 40 to 80 mg/ml. Generally, the bis salt will have a lower aqueous solubility than the corresponding mono salt, but in either case the aqueous solubility is relatively higher than that of the free fatty acid or ester form of the fatty acid. In one embodiment, a compound of the invention has an aqueous solubility that is about 2-fold, about 5-fold, or about 10-fold higher, or more, than that of the free fatty acid or ester form of the fatty acid.

In one embodiment, a compound of the invention provides a solubility of the fatty acid component in aqueous solution that is from about 50 to 100 times greater than the solubility of the ethyl ester form of the fatty acid.

The compounds of the invention having a fatty acid component may also demonstrate improved physical stability compared to, for example, the ethyl ester form of the fatty acid. In certain embodiments, the compounds of the invention also provide for increased stability against oxidative degradation of the fatty acid component.

Pharmacokinetic Properties

The compounds of the invention demonstrate highly favorable pharmacokinetic properties. For example, the compounds having a fatty acid molecule in the counter-ion component provide high levels of serum free fatty acids following oral or intravenous administration, as discussed in more detail in the examples, infra. The present invention provides what is believed to be the first instance of a compound that is suitable for administrating fatty acids by the intravenous route. The poor water solubility of fatty acids in general has contraindicated their use in intravenous formulations. In addition, the compounds of the invention formulated as oral dosage forms deliver much higher amounts of the free fatty acid component to the serum than is achievable with oral administration of, for example, the free fatty acid itself or the ethyl ester form of the fatty acid. These properties are further discussed and exemplified in the examples, infra.

Compositions

The compounds of the invention may be formulated into pharmaceutical compositions for human or animal use. In one embodiment, the compounds are formulated into a pharmaceutical composition comprising a pharmaceutically acceptable carrier, and optionally one or more pharmaceutically acceptable excipients.

The term "excipient" refers to an additive that serves some purpose in the composition other than a carrier, for example as a stabilizer, taste masking agent (e.g., a sweetener), solubilizing agent, or suspending agent. Often, a carrier will serve a dual purpose as a simple carrier or diluent and an excipient. Examples of pharmaceutically acceptable excipients may thus include carriers. Non-limiting examples of excipients for use in the compositions of the invention include sterile liquids, water, buffered saline, ethanol, polyols (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures thereof.

A suitable excipient or carrier is typically a pharmaceutically acceptable carrier or excipient for use in animals or humans (or both). The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. In the context of the pharmaceutical compositions of the invention, a "carrier" refers to, for example, a solvent, a diluent, or vehicle with which the ionic salt of the invention is formulated for delivery.

Examples of pharmaceutically acceptable carriers for use in the compositions of the invention include, without limitation, sterile aqueous and non-aqueous liquids, water, buffered saline, ethanol, polyols (for example, glycerol, propylene glycol, liquid polyethylene glycol and the like), and oils, for liquid dosage forms; or carbohydrates (e.g., glucose, lactose, sucrose or dextran) for solid dosage forms.

Further examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyllaurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The compositions of the invention may be formulated in any suitable form and for any suitable intended route of administration. Typically, the dosage form is at least in part determined by the intended route of administration. In one embodiment, the dosage form is an oral dosage form. The oral dosage form may be in the form of a solid, such as a tablet, a capsule containing particulates, liquids, or powders, a lozenge (including liquid-filled), a gum, or a gel, or in the form of a liquid. In one embodiment, the dosage form is a solid oral dosage form.

In another embodiment, the pharmaceutical composition of the invention is formulated as a gel or cream suitable for topical administration.

A composition of the invention may be in the form of a unit dose. The unit dose may be, for example, in the form of a tablet or capsule.

Intravenous Formulations

In one embodiment, the pharmaceutical composition of the invention is formulated as an intravenous dosage form. In one embodiment, the intravenous dosage form is in the form of a clear solution. In one embodiment the composition is in the form of a lyophilized solid in an ampule suitable for reconstitution with sterile water-for-injection or aqueous buffer for intravenous administration. In one embodiment, the composition is in the form of a nutritional formula for administration of total parenteral nutrition.

Ophthalmic Formulations

In one embodiment, A or B, or both, are useful for treating or ameliorating one or more symptoms of an ocular disease or disorder, as described in more detail below. Accordingly, the invention provides compounds of Formula I in a pharmaceutical composition of the invention suitable for topical administration to the eye, also referred to as an ophthalmic formulation. The formulation may be a solution, suspension, or gel suitable for ocular administration.

In one embodiment, the ophthalmic formulation is an aqueous formulation. In one embodiment, the ophthalmic formulation comprises one or more of glycerin, hypromellose, propylene glycol or polyethylene glycol. In one embodiment, the ophthalmic formulation further comprises one or more of polysorbate 80, carbomer copolymer type A, purified water, sodium hydroxide, ascorbic acid, benzalkonium chloride, boric acid, dextrose, disodium phosphate, glycine, magnesium chloride, potassium chloride, sodium borate, sodium chloride, sodium citrate, sodium lactate, edetate disodium, hydrochloric acid, sodium hydroxide, aminomethylpropanol, hydroxypropyl guar, polyquaternium-I, or sorbitol.

In one embodiment, the ophthalmic formulation comprises one or more of surfactants, tonicity agents, buffers, preservatives, co-solvents and viscosity building agents. Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Preferably, the tonicity agent is present in an amount sufficient to cause the final composition to have an ophthalmically acceptable osmolality (generally about 150-450 mOsm, preferably 250-350 mOsm). An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6-7.5.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more of the fatty acid salts of the invention.

Examples or artificial tears compositions useful as artificial tears carriers include, but are not limited to, commercial products, such as Tears Naturale™, Tears Naturale n™, Tears Naturale Free™, and Bion Tears™. (Alcon Laboratories, Inc., Fort Worth, Tex.). Examples of phospholipid carrier formulations include those disclosed in U.S. Pat. Nos. 4,804,539 (Guo et al.), 4,883,658 (Holly), 4,914,088 (Glonek), 5,075,104 (Gressel et al.), 5,278,151 (Korb et al.), 5,294,607 (Glonek et al.), 5,371,108 (Korb et al.), 5,578,586 (Gionek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as polyvinyl alcohol, polyvinylpyrrolidone, povidone and carbomers, such as carbomer 934P, carbomer 941, carbomer 940, carbomer 974P.

Examples of viscosity enhancing agents include, but are not limited to polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears will exhibit a viscosity of 1 to 400 centipoises ("cps"). Topical ophthalmic products are typically packaged in multidose form. Preservatives may be required to prevent microbial contamination during use. Suitable preservatives include benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Other wetting agents, emulsifiers and lubricants, such as sodium lauryl sulfate and magnesium stearate, as well as coloring agents, release agents, coating agents, and perfumingagents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, a-tocopherol, and the like; and metal chelating agents, such as citric acid, ethylenediamine tetraacetic acid (EDT A), sorbitol, tartaric acid, phosphoric acid, and the like.

A contact lens may optionally be used to allow for extravasation of vasoactive substance over a more prolonged time period. Vasoactive substances such as Thrombin and Thromboxane A may further induce increase in tear volume via venular vasoconstriction and increased perfusion through lacrimal, accessory lacrimal and surface microvessels; where increased paracellular endothelial openings that increase capillary permeability can further enhance this benefit.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers.

Additives and Supplements

In one embodiment, A or B, or both are useful as a dietary supplement or nutraceutical additive. For example, fatty acids, especially polyunsaturated fatty acids of the omega-3, omega-6, omega-7, and omega-9 series are known to be useful in this context. Thus, the invention also provides a compound of Formula I formulated as a nutraceutical additive or supplement, either alone or in combination with one or more additives or supplements and any suitable excipients. In one embodiment, the nutraceutical additive or supplement is in the form of a powder. In one embodiment, the nutraceutical additive or supplement is in the form of a liquid. In one embodiment, the nutraceutical additive or supplement is in the form of a mouth wash, a dentifrice, chewing gum, a candy, a tablet, a capsule, a mouth spray, or a film.

In one embodiment, the nutraceutical additive forms part of a food or drink product suitable for human consumption. There is no specific limitation on the foods/drinks to which a nutraceutical additive of the invention can be incorporated. Examples of such foods/drinks include processed foods based on meat, poultry meat, fish/shellfish and the like; soup; seasonings including sweetener and the like; rice seasonings; instant foods; frozen foods; snacks; various types of functional foods such as supplements, nutritional drinks and the like; canned foods; dairy products; confectionery such as chewing gum, candy, gummy candy, chocolate, baked sweets and the like; ice cream; soft drinks such as tea, coffee, cocoa, fruit juice, sports drink, carbonated drink, vegetable drink and the like; liquors; soya milk; lactic acid bacteria beverages; and chlorophyll juice.

The amount of the nutraceutical additive of the invention incorporated into the food or drink varies in accordance with the type of food or drink and the amount that one wishes to supplement a diet with one or more omega-3 fatty acids. In one embodiment, the nutraceutical additive is incorporated into the food or drink so as to provide an amount of the omega-3 fatty acid that is about 0.000001 to 20% by weight, based on total weight of the food or drink product, and more preferably in an amount of about 0.00001 to 10% by weight.

Methods of Making

The compounds of the present invention can be prepared according to the general Scheme 1 and as further exemplified in Scheme 2. Further details for the preparation of the compounds are provided in the Examples section, infra.

Scheme 1

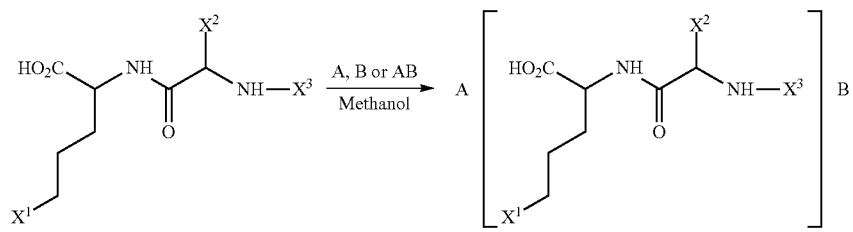

Scheme 2

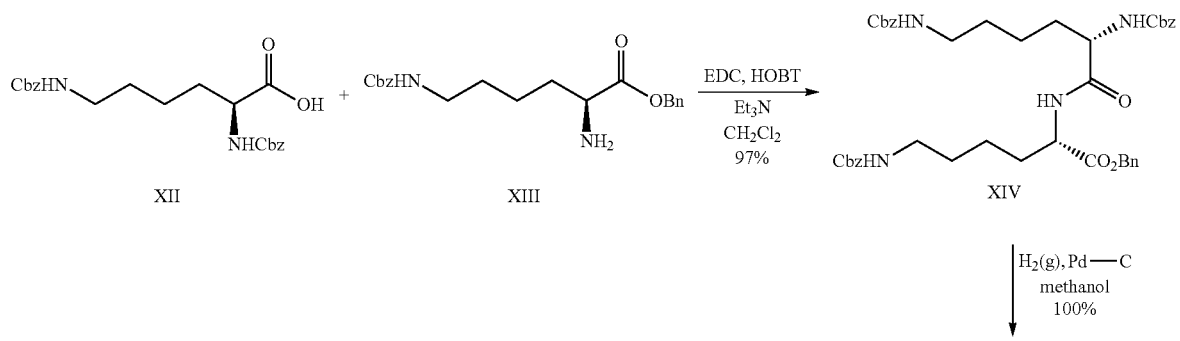

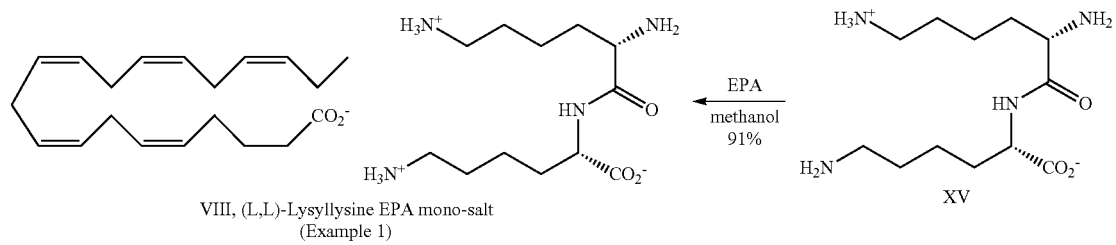

VIII, (L,L)-Lysyllysine EPA mono-salt
(Example 1)

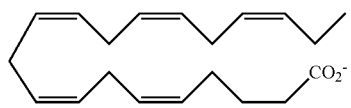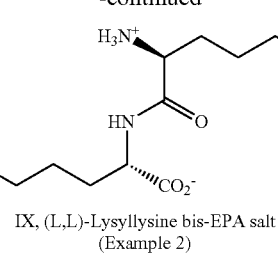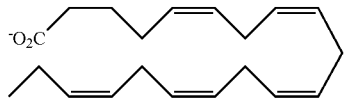

IX, (L,L)-Lysyllysine bis-EPA salt
(Example 2)

Methods of Use

The compositions of the invention are useful in methods of treating various diseases and disorders that are responsive to treatment with fatty acids, especially polyunsaturated fatty acids, and particularly polyunsaturated fatty acids of the omega-3, omega-6, omega-7, and omega-9 series. In the context of any of the methods described here, a composition of the invention may be formulated as a pharmaceutical composition, meaning that the composition itself and any additives or excipients in the formulation are suitable for administration to humans or animals.

In the context of the methods described here, the term "treating" may refer to the amelioration or stabilization of one or more symptoms associated with the disease or disorder. The term "treating" may also encompass the management of a disease or disorder, referring to the beneficial effects that a subject derives from a therapy which does not result in a cure of the underlying disease or disorder. For example, lowering elevated plasma triglycerides can be considered an aspect of treating diabetes because it is a beneficial effect that does not result in a cure of the underlying defect of glucose metabolism. The compositions of the invention can also be used in the prevention of certain diseases, disorders, and conditions. In this context, the term "prevention" refers to preventing the recurrence, development, progression or onset of one or more symptoms of the disease, disorder, or condition.

In accordance with the methods of the invention, a therapeutically effective amount of a composition of the invention is administered to a subject, preferably a human subject, the therapeutically effective amount being the amount sufficient to achieve a desired therapeutic outcome, for example the amelioration or stabilization of one or more symptoms of the disease or disorder being treated, or in the context of prevention, the amount sufficient to achieve prevention of the recurrence, development, progression or onset of one or more symptoms of the disease, disorder, or condition.

For administration to human patients, the total daily dose of the compounds of the invention is typically in the range 1 g to 12 g depending, of course, on the mode of administration. In one embodiment the total daily dose is in the range 1 g to 10 g, in another embodiment the total daily dose is in the range 4 g to 8 g and in yet another embodiment the total daily dose is in the range 1 g to 2 g. The total daily dose may be administered in single or divided doses.

These dosages are based on an average human subject having a weight of about 65 kg to 70 kg. The physician will readily be able to determine doses for subjects whose weight falls outside this range, such as infants and the elderly.

In one embodiment, a therapeutically effective amount is the amount required to achieve at least an equivalent therapeutic effect compared to a standard therapy. An example of a standard therapy is an FDA-approved drug indicated for treating a particular disease or disorder. As an example, Vascepa™ is an FDA-approved formulation of EPA, specifically an ethyl ester of EPA. Thus, in one embodiment, the invention provides a pharmaceutical composition comprising a compound of Formula I having one or two EPA molecules as the counter-ion component in a therapeutically effective amount, which amount is effective to reduce plasma triglycerides in an adult human subject by at least about 0.5 mmol/L, about 1 mmol/L, or about 2 mmol/L.

In the context of any of the methods of the present invention, the subject may be a human or a non-human mammal The non-human mammal may be, for example, a non-human primate, a dog, cat, a rodent (e.g., a mouse, a rat, a rabbit), a horse, a cow, a sheep, a goat, a bird, a chicken, or any other non-human mammal Preferably, the subject is a human.

In one embodiment, the subject is a human subject. In one embodiment, the human is an adult human, a pediatric human, or a geriatric human, as those terms are understood by the medical practitioner, for example as defined by the U.S. Food and Drug Administration.

The compositions of the invention can be used as monotherapy or adjunctive therapy. The compositions of the invention can be administered alone or in combination with one or more additional therapeutic agents (i.e., additional APIs) or therapies, for example as part of a therapeutic regimen that includes, e.g., aspects of diet and exercise. In certain embodiments, the methods of the invention include administration of a composition of the invention as the primary therapy. In other embodiments, the administration of a composition of the invention is an adjuvant therapy. In either case, the methods of the invention contemplate the administration of a composition of the invention in combination with one or more additional therapeutic agents and/or therapies for the treatment or prevention of a disease or disorder. The terms "therapy" and "therapies" refer to any method, protocol and/or agent that can be used in the prevention, treatment, management or amelioration of a disease or disorder, or one or more symptoms thereof.

Metabolic Disorders

In one embodiment, the invention provides methods of treating a metabolic disorder in a subject in need thereof, the method comprising administering to the subject, preferably a human subject, a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA).

In one embodiment the metabolic disorder is selected from the group consisting of abnormal glucose metabolism manifesting in diabetes or pre-diabetes, abnormal lipid metabolism manifesting as hypertriglyceridemia, i.e., elevated triglycerides, mixed dyslipidemia, hypercholesterolemia, fatty liver, and combined abnormal glucose and lipid metabolism manifesting in obesity. In one embodiment the metabolic disorder is a dyslipidemic disorder selected from hypertriglyceridemia, hypercholesterolemia and mixed dyslipidemias. In one embodiment, the metabolic disorder is selected from the group consisting of pre-diabetes, type 2 diabetes, obesity, fatty liver disease, and insulin resistance.

In one embodiment, the methods comprise administering a therapeutically effective amount, which amount is effective to reduce plasma triglycerides in an adult human subject by at least about 0.5 mmol/L, about 1 mmol/L, or about 2 mmol/L.

In one embodiment, the subject is a human subject having severe hypertriglyceridemia characterized by serum triglyceride levels of from 500 to 2,000 mg/dl.

Cardiovascular Disorders

In one embodiment, the invention provides a method for treating cardiovascular disorders or complications relating to atrial fibrillation, myocardial infarction, and congestive heart failure by administering to a subject in need of such treatment an effective amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA). In one embodiment, the effective amount is effective to treat one or more symptoms of the cardiovascular condition.

Gastrointestinal Disorders

In one embodiment, the invention provides a method for treating gastrointestinal disorders or complications relating to parenteral nutrition-associated liver disease, and essential fatty acid deficiency and other pediatric GI disorders including congenital GI anomalies and necrotizing enterocolitis by administering to a subject in need of such treatment an effective amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA). In one embodiment, the effective amount is effective to treat one or more symptoms of the gastrointestinal condition.

In one embodiment, the invention provides a method for providing nutrition to patients who do not have a functioning gastrointestinal tract or who have disorders requiring complete bowel rest, including bowel obstruction, short bowel syndrome, Gastroschisis, prolonged diarrhea regardless of its cause, high-output fistula, and very severe Crohn's disease or ulcerative colitis by administering to a subject in need of such treatment an effective amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA). In one embodiment, the effective amount is effective to treat one or more symptoms of the gastrointestinal condition.

In one embodiment, the invention provides a method for preventing cancer, the method comprising administering a therapeutically effective amount of a composition of the invention to a subject in need of preventive anti-cancer therapy. In one embodiment, the cancer is colon cancer or familial adenomatous polyposis.

Inflammatory Disorders

The compounds of Formula I having one or two polyunsaturated fatty acid molecules as the counter-ion component may be particularly useful in the treatment of diseases and disorders having a significant inflammatory component, due to the anti-inflammatory properties of polyunsaturated fatty acids and the ability of the compounds of Formula I to deliver high amounts of free fatty acids to the serum by either oral or intravenous routes of administration.

In one embodiment, the invention provides a method for treating an inflammatory disorder, the method comprising administering to a subject in need of such treatment an effective amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA). In one embodiment, the effective amount is effective to treat one or more symptoms of the inflammatory disorder. In one embodiment, the inflammatory disorder is selected from the group consisting of arthritis, inflammatory bowel disease, and psoriasis.

In one embodiment, the invention provides methods of treating arthritis, irritable bowel syndrome, ophthalmic inflammation disorders, or dry eye syndrome in a subject in need of such treatment, the methods comprising administering to the subject a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA).

In one embodiment, the invention provides a method for treating a disease or disorder of the ocular system, also referred to as ophthalmic diseases and disorders, having an underlying inflammatory component, the method comprising administering to a subject in need of such treatment an effective amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA). In one embodiment, the effective amount is effective to treat one or more symptoms of the disease or disorder of the ocular system. In one embodiment, the disease or disorder of the ocular system is selected from the group consisting of inflammatory diseases of the eye, dry eye syndrome, macular edema and retinopathy. In one embodiment, the method is a method for promoting corneal wound healing.

In one embodiment, the invention provides a method for treating dry eye by administering a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA). Dry eye disease or syndrome is a multifactorial disorder of the tears and ocular surface characterized by symptoms of dryness and irritation. Inflammation is an important component in the development and propagation of dry eye (Stevenson et al., Arch. Ophthalmol., 2012, 130 (1), 90-100; Rashid et al., Arch. Ophthalmol, 2008, 126 (2), 219-225).

The term "dry eye" refers to inadequate tear production and/or abnormal tear composition. Causes of dry eye disease as defined herein include but are not limited to the following: idiopathic, congenital alacrima, xerophthalmia, lacrimal gland ablation, and sensory denervation; collagen vascular diseases, including rheumatoid arthritis, Wegener's granulomatosis, and systemic lupus erythematosus; Sjogren's syndrome and autoimmune diseases associated with Sjogren's syndrome; abnormalities of the lipid tear layer caused by blepharitis or rosacea; abnormalities of the mucin tear layer caused by vitamin A deficiency; trachoma, diphtheric keratoconjunctivitis; mucocutaneous disorders; aging; menopause; and diabetes. Further, the term "dry eye" includes dry eye after anterior ophthalmic operation such as cataract operation and refractive surgery and that accompanied with allergic conjunctivitis Dry eye symptoms as defined herein may also be provoked by other circumstances, including, but not limited to, the following: prolonged visual tasking; working on a computer; being in a dry environment; ocular irritation; contact lenses, LASIK and other refractive surgeries; fatigue; and medications such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine.

Neurological Disorders

In one embodiment, the invention provides a method for treating a psychiatric disorder in a subject, the method comprising administering the subject a therapeutically effect amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA), where the amount is effective to treat one or more symptoms of the psychiatric disorder. In one embodiment, the psychiatric disorder is selected from Alzheimer's disease, attention deficit hyperactivity disorder (ADHD) and depression.

In one embodiment, the invention provides a method for treating a neuro trauma injury in a subject, the method comprising administering to the subject a therapeutically effective amount of a composition comprising a compound of Formula I having one or two polyunsaturated fatty acid molecules as the counter-ion component. In one embodiment, the polyunsaturated fatty acid molecules are of the omega-3, omega-6, omega-7, or omega-9 series. In one embodiment, the fatty acid molecules are omega-3 fatty acids independently selected from eicosapentaenoic acid (EPA), docosahexaenoic acid (DHA), and docosapentaenoic acid (DPA), where the amount is effective to treat one or more symptoms of the neuro trauma injury. In one embodiment, the neuro trauma injury is selected from traumatic brain injury, spinal cord injury, ischemic stroke, and concussion.

In one embodiment, the invention provides a method for treating epilepsy or epileptic syndrome by administering to a subject in need of such treatment a composition comprising a compound of Formula I having one or two gabapentin molecules as the counter-ion component. In one embodiment, the method comprises administering to the subject in need of treatment for epilepsy or epileptic syndrome a composition of the invention which has been formulated to contain at least one additional API in a single dosage form. In one embodiment, the additional API is an anti-epileptic agent such as gabapentin, or a pharmaceutically acceptable salt and prodrug thereof.

Pain

In one embodiment, the invention provides a method for treating or managing pain. In one embodiment, the pain is neuropathic pain and the method comprises administering to a subject in need of treatment for neuropathic pain a pharmaceutical composition comprising a compound of Formula I wherein A and B are both present, A or B is a polyunsaturated fatty acid, for example, EPA, DHA, or DPA, and the other molecule of the counter-ion component is a non-steroidal anti-inflammatory agent (NSAID), or a pharmaceutically acceptable salt or prodrug thereof.

In one embodiment, the pain is nociceptive pain and the method comprises administering to a subject in need of treatment for nociceptive pain a pharmaceutical composition comprising a compound of Formula I wherein A and B are both present, A or B is a polyunsaturated fatty acid, for example, EPA, DHA, or DPA, and the other molecule of the counter-ion component is gabapentin, or a pharmaceutically acceptable salt or prodrug thereof.

In one embodiment, the method comprises administering to the subject in need of treatment for neuropathic pain a composition of the invention which has been formulated to contain at least one additional active pharmaceutical agent (API) in a single dosage form. In one embodiment, the additional API is a NSAID, or a pharmaceutically acceptable salt or prodrug thereof. In another embodiment, the pain is nociceptive pain and the method comprises administering a composition of the invention to a subject in need of treatment for nociceptive pain. In one embodiment, the method comprises administering to the subject in need of treatment for nociceptive pain a composition of the invention which has been formulated to contain at least one additional API in a single dosage form. In one embodiment, the additional API is gabapentin, or a pharmaceutically acceptable salt or prodrug thereof.

Combination Therapies

In the context of combination therapies, a composition of the invention may be administered together with at least one additional API or separately from the additional API. Where delivery is together, a composition of the invention may be delivered in the same dosage form as the additional API, or in a different dosage form. One of the advantages of the present invention, as discussed above, is the ease of formulating the compositions described herein with additional APIs and excipients in a single solid dosage form due to their form as a free flowing powder that is chemically and physically stable (as opposed to the relatively unstable oily liquid form of free fatty acids and their esters).

In one embodiment, a composition of the invention is formulated in a single solid dosage form with an antihyperlipidemic agent or an anti-diabetic agent. Antihyperlipidemic agents that may be used include HMG CoA enzyme inhibitors (e.g., statins), cholesterol absorption inhibitors, and cholesterol esterase transfer protein (CETP) inhibitors. In one embodiment, the antihyperlipidemic agent is selected from a statin, a cholesterol absorption inhibitor, a CETP inhibitor, and pharmaceutically-acceptable salts and prodrugs of any of the foregoing. The pharmaceutically acceptable salt may be selected from the group consisting of a propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, p-hydroxybutyrate, glycolate, tartrate, methanesulfonate, propanesulfonates, naphthalene-1-sulfonate, naphthalene-2-sulfonate, mandelate, hippurate, gluconate, and lactobionate salt.

In one embodiment, the antihyperlipidemic agent is a statin. In one embodiment, the statin is selected from the group consisting of atorvastatin, risuvostatin, simvastatin, pravastatin, and pharmaceutically acceptable salts and prodrugs of any of the foregoing. In one embodiment, the statin is present in an amount ranging from 5 mg to 100 mg. In one embodiment, the statin is pravastatin.

In one embodiment, the antihyperlipidemic agent is a cholesterol absorption inhibitor. In one embodiment, the cholesterol absorption inhibitor is ezetimibe, also known as Zetia.

In one embodiment, the antihyperlipidemic agent is a CETP inhibitor. In one embodiment, the CETP inhibitor is anacetrapib, or a hydrate, or solvate thereof.

In one embodiment, a composition of the invention is formulated in a single solid dosage form with an anti-epileptic agent or an inhibitor of neuropathic pain such as gabapentin, or a pharmaceutically acceptable salt and prodrug thereof.

The invention is further described in the following examples, which do not limit the scope of the invention described in the claims.

EXAMPLES

Table 2 shows a number of specific examples of the compounds described herein.

TABLE 2

| Compound # | Structure | Name |
|---|---|---|
| 1 | [Structure of lysyl-lysine with one EPA carboxylate] | (L,L) Lysyl-lysine EPA salt (mono) |
| 2 | [Structure of lysyl-lysine with two EPA carboxylates] | (L,L) Lysyl-lysine bis-EPA |
| 3 | [Structure of lysyl-lysine with one DHA carboxylate] | (L,L) Lysyl lysine DHA (mono) |

TABLE 2-continued
Compounds
| Compound # | Structure | Name |
|---|---|---|
| 4 | 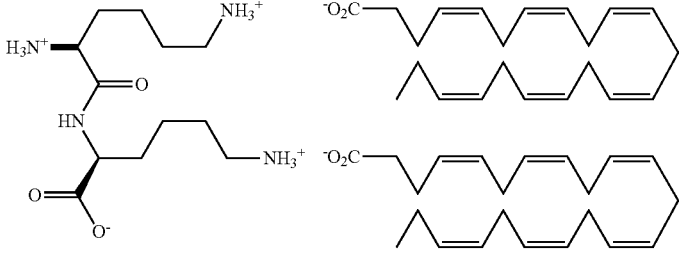 | (L,L) Lysyl-lysine bis DHA |
| 5 | 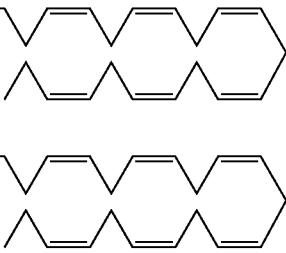 | (L,L) Lysyl-lysine EPA DHA |
| 6 | 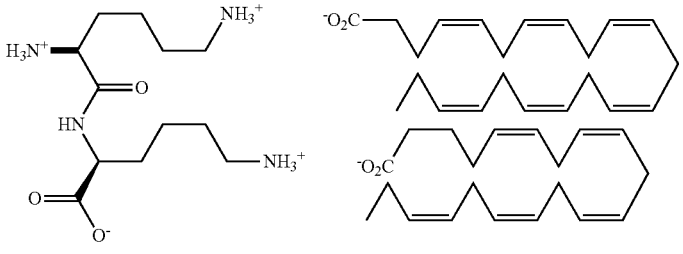 | (L,L) Lysyl-lysine bis gabapentin |
| 7 | 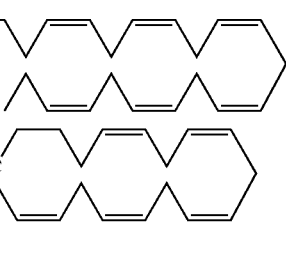 | (L,L) Lysyl-lysine EPA niacin |
| 8 | 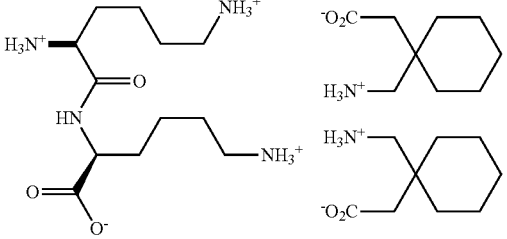 | (L,L)-lysyl-lysine EPA ibuprofen |

TABLE 2-continued

Compounds

| Compound # | Structure | Name |
|---|---|---|
| 9 | 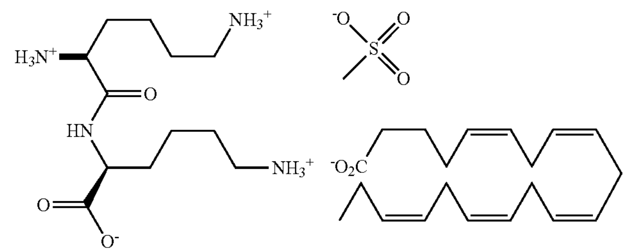 | (L,L)-lysyl-lysine EPA methanesulfonic acid salt |
| 10 | 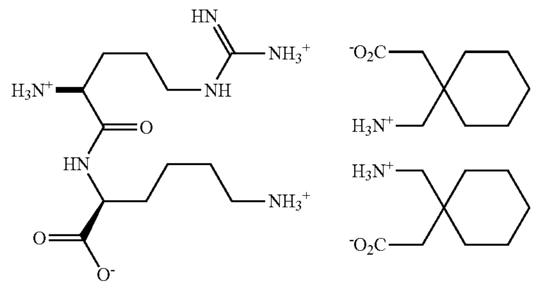 | (L,L) arginyl-lysine bis gabapentin |
| 11 | 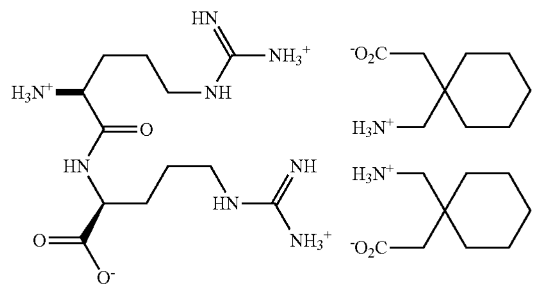 | (L,L) arginyl-arginine bis gabapentin |

Experimental Procedures for Making Compounds 1-11

The following precursors are used in making Compounds 1-11.

a. benzyl N6-((benzyloxy)carbonyl)-N2-(N2,N6-bis((benzyloxy)carbonyl)-L-lysyl)-L-lysinate

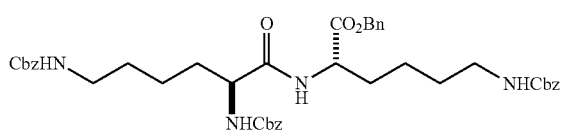 [SMILES: O=C(NCCCC[C@H](NC(=O)OCc1ccccc1)C(=O)N[C@@H](CCCCNC(=O)OCc1ccccc1)C(=O)OCc1ccccc1)OCc1ccccc1]

A solution/suspension of H-Lys(Z)-OBzl hydrochloride (16.3 g, 40 mmol) and Z-Lys(Z)—OH (16.6 g, 40 mmol) in anhydrous dichloromethane (50 mL) under nitrogen was cooled on ice and treated with HOBT hydrate (9.2 g, 60 mmol) and triethylamine (16.8 mL, 120 mmol), and the clear solution was stirred for 15 min. EDC hydrochloride (9.6 g, 50 mmol) was added, and the stirred mixture allowed to warm to room temperature and stirred 20 h. The product mixture was diluted to 500 mL total volume with dichloromethane, then washed successively with 5% citric acid, water, saturated aqueous sodium bicarbonate, and brine (200 mL each), and dried (Na$_2$SO$_4$). The solution was added directly to a silica gel column (~500 cc) and eluted with dichloromethane, then 2:1 dichloromethane/ethyl acetate to afford 29.71 g (97%) of subject material as a white solid. MP 145-6° C. NMR (CDCl$_3$): δ 7.15-7.30 (m, 20H), 6.50-6.65 (m, 1H), 5.40-5.55 (m, 1H), 5.10 (d, 1H, J=11.5 Hz), 4.90-5.10 (m, 8H), 4.45-4.55 (m, 1H), 4.05-4.15 (m, 1H), 2.90-3.15 (m, 4H), 1.70-1.80 (m, 2H), 1.55-1.65 (m, 2H), 1.10-1.45 (m, 8H). $^{13}$C NMR (151 MHz, cdcl$_3$) δ 171.94, 156.68, 156.59, 156.33, 136.59, 136.50, 136.15, 135.23, 128.60, 128.59, 128.50, 128.48, 128.47, 128.37, 128.34, 128.16, 128.09, 128.04, 76.82, 67.21, 67.05, 66.69, 66.60, 54.50, 52.14, 40.22, 40.17, 32.06, 31.25, 29.17, 22.14, 22.04.

b. L-lysyl-L-lysine

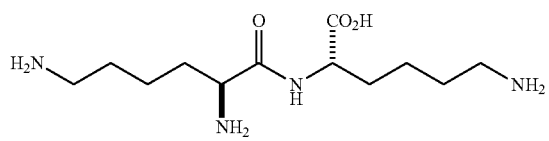 [SMILES: NCCCC[C@H](NC(=O)[C@@H](N)CCCCN)C(=O)O]

A stirred solution/suspension of (L,L)-Z3-lysyllisine, benzyl ester (5.37 g, 7.0 mmol) in methanol (120 mL) under nitrogen was treated with 10% Pd/C (0.50 g), then evacuated and purged several times with hydrogen via balloon. The mixture was stirred for 42 h under hydrogen, then the flask evacuated with nitrogen and carefully filtered through Celite with water rinse. The filtrate was concentrated in vacuo to afford a white foam. The foam was transferred to a 50 mL pear shaped flask by dissolving in hot methanol, then concentrated in vacuo and the residual foam stirred with acetonitrile for 30 min, filtered, collected, and dried in vacuo to afford 1.92 g (100%) as a white powder. MP 88-90° C. NMR (D$_2$O): δ 4.08 (dd, 1H, J=5 Hz, 8 Hz), 3.31 (t, 1H, J=7 Hz), 2.75-2.95 (m, 4H), 1.45-1.80 (m, 8H), 1.20-1.40 (m, 4H). $^{13}$C NMR (151 MHz, d$_2$o) δ 178.75, 176.84, 54.77, 54.26, 40.95, 39.40, 33.72, 31.12, 27.66, 27.11, 22.14, 21.80.

c. benzyl N6-((benzyloxy)carbonyl)-N2-(N2,Nd,Nw-tris((benzyloxy)carbonyl)-L-arginyl)-L-lysinate

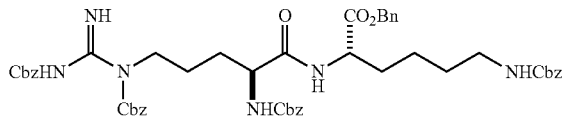 [SMILES: N=C(NC(=O)OCc1ccccc1)N(CCC[C@H](NC(=O)OCc1ccccc1)C(=O)N[C@@H](CCCCNC(=O)OCc1ccccc1)C(=O)OCc1ccccc1)C(=O)OCc1ccccc1]

A solution/suspension of H-Lys(Z)-OBzl hydrochloride (4.07 g, 10 mmol) and Z2-Arg(Z)—OH (5.77 g, 10 mmol) in anhydrous dichloromethane (50 mL) under nitrogen was cooled on ice and treated with HOBT hydrate (2.3 g, 15 mmol) and triethylamine (4.2 mL, 30 mmol), and the clear solution was stirred for 15 min. EDC hydrochloride (2.40 g, 12.5 mmol) was added, and the stirred mixture allowed to warm to room temperature and stirred 20 h. The above mixture was diluted with dichloromethane to 250 mL, washed with 5% citric acid (100 mL), then water, saturated sodium bicarbonate, and brine (50 mL each), dried (Na2SO4) and concentrated in vacuo. The residual amorphous solid was triturated from acetonitrile to afford 7.40 g (80%) as an amorphous white solid. NMR (CDCl3): □□9.41-9.28 (m, 3H), 7.38-7.19 (m, 25H), 6.87 (br s, 1H), 6.09-6.07 (m, 1H), 5.22 (s, 2H), 5.16-4.92 (m, 8H), 4.51-4.47 (m, 1H), 4.38-4.32 (m, 1H), 3.98-3.83 (m, 2H), 3.03-2.98 (m, 2H), 1.74-1.60 (m, 5H), 1.44-1.29 (m, 3H), 1.20-1.13 (m, 2H)

d. L-arginyl-L-lysine

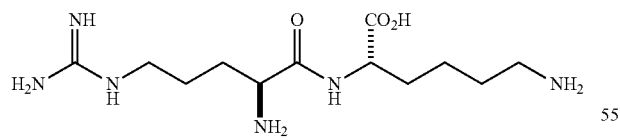

A stirred solution/suspension of benzyl N6-((benzyloxy)carbonyl)-N2-(N2,Nd,Nw-tris((benzyloxy)carbonyl)-L-arginyl)-L-lysinate (6.97 g, 7.5 mmol) in methanol (125 mL) under nitrogen was treated with 20% Pd(OH)2/C (0.50 g, Pearlman's catalyst), then evacuated and purged several times with hydrogen via balloon. The mixture was stirred for 48 h at 45° C., then the flask cooled and evacuated with nitrogen, diluted with water (125 mL) and re-purged with hydrogen via balloon (gray precipitate still present indicating incomplete deprotection). Stirring was continued for 16 h more, after which only charcoal could be seen in suspension. The flask was cooled and evacuated with nitrogen, then the contents carefully filtered through Celite with water rinse. The filtrate was concentrated in vacuo to afford 2.27 g (100%) as a white foam. NMR (D$_2$O): δ 3.97 (dd, 1H, J=5 Hz, 8 Hz), 3.85 and 3.24 (1H, both m, rotamers), 3.02-2.97 (m, 2H), 2.80-2.70 (m, 2H), 1.65-1.38 (m, 8H), 1.25-1.17 (m, 2H).

e. Nd,Nw-bis((benzyloxy)carbonyl)-N2-(tert-butoxycarbonyl)-L-arginine

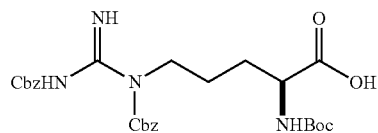 [SMILES: CC(C)(C)OC(=O)N[C@@H](CCCN(C(=N)NC(=O)OCc1ccccc1)C(=O)OCc1ccccc1)C(=O)O]

A stirred solution of Nα-Boc-arginine hydrochloride hydrate (9.86 g, 30 mmol) in methanol (50 mL) was treated with 30% sodium methoxide (5.20 g, 30 mmol), then stirred a few minutes and filtered. The filtrate was concentrated in vacuo and the residual foam was treated with toluene (3×30 mL) and three times concentrated in vacuo to remove all methanol. The residual material was suspended with stirring in anhydrous 1,2-dichloroethane (75 mL) under nitrogen and treated with N,N-diisopropylethylamine (18.3 mL, 105 mmol). Chlorotrimethylsilane (13.4 mL, 105 mmol) was then added at a rate to keep pot temperature below 35° C., and the mixture was heated to 40° C. for 1.5 h, then cooled on ice. Additional N,N-diisopropylethylamine (15.7 mL, 90 mmol) was added, followed by benzyl chloroformate (12.85 mL, 90 mmol) in one portion, and the mixture was stirred on ice for 15 min, allowed to warm to room temperature over 30 min, and stirred at room temperature for 4 h. The reaction mixture was plunged into 15% citric acid (200 mL) and stirred for 15 min, then extracted with dichloromethane (150 mL, then 2×50 mL). The combined organic solution was washed with water and brine (100 mL each), dried (Na$_2$SO$_4$), and concentrated in vacuo. The residual oil was dissolved in dichloromethane and added to a silica gel column (~600 cc) and eluted with 10% ethyl acetate/dichloromethane (this gave 0.90 g of lactam byproduct), then 6% ethanol/dichloromethane to afford (after solidification with a small amount of ether and drying in vacuo) 8.11 g (50%) of as a white solid. NMR (CDCl$_3$): δ 9.43-9.28 (m, 2H), 7.39-7.26 (m, 10H), 5.28-5.26 (m, 1H), 5.22 (s, 2H), 5.12 (s, 2H), 4.28-4.24 (m, 1H), 3.99-3.95 (m, 2H), 1.82-1.63 (m, 4H), 1.39 (s, 9H).

f. benzyl Nd,Nw-bis((benzyloxy)carbonyl)-N2-(N2,Nd,Nw-tris((benzyloxy)carbonyl)-L-arginyl)-L-argininate

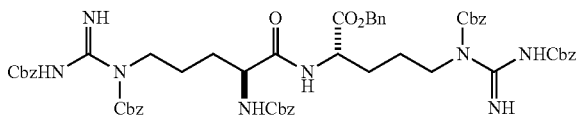 [SMILES: N=C(NC(=O)OCc1ccccc1)N(CCC[C@H](NC(=O)OCc1ccccc1)C(=O)N[C@@H](CCCN(C(=N)NC(=O)OCc1ccccc1)C(=O)OCc1ccccc1)C(=O)OCc1ccccc1)C(=O)OCc1ccccc1]

A solution/suspension of benzyl N$^δ$,N$^ω$-bis((benzyloxy)carbonyl)-L-argininate (6.64 g, 12.47 mmol) and Z2-Arg(Z)—OH (7.19 g, 12.47 mmol) in anhydrous dichloromethane (60 mL) under nitrogen was cooled on ice and treated with HOBT hydrate (2.87 g, 18.7 mmol) and triethylamine (3.9 mL, 28 mmol), and the clear solution was stirred for 15 min. EDC hydrochloride (3.00 g, 15.65 mmol) was added, and the stirred mixture allowed to warm to room temperature and stirred 20 h. The above mixture was diluted with dichloromethane to 250 mL, washed with 5% citric acid (100 mL), then water, saturated sodium bicarbonate, and brine 75 mL each), dried (Na2SO4) and filtered. The filtrate was added directly to a silica gel column (~400 cc) and eluted with 9:1 dichloromethane/ethyl acetate to afford 8.34 g (61%) as a white solid. NMR (CDCl$_3$): δ 9.13 (br s, 4H), 8.31 (d, 1H, J=7.5 Hz), 7.38-7.15 (m, 30H), 5.17-5.13 (m, 4H), 5.02-4.92 (m, 8H), 4.46 (d, 1H, J=5.5 Hz), 4.27-4.23 (m, 1H), 4.02-3.97 (m, 1H), 3.94-3.70 (m, 4H), 1.70-1.35 (m, 8H)

g. benzyl Nd,Nw-bis((benzyloxy)carbonyl)-N2-(tert-butoxycarbonyl)-L-argininate

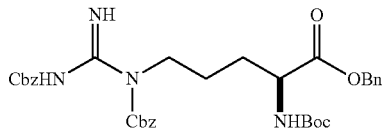 [SMILES: CC(C)(C)OC(=O)N[C@@H](CCCN(C(=N)NC(=O)OCc1ccccc1)C(=O)OCc1ccccc1)C(=O)OCc1ccccc1]

A cooled (0° C.) stirred solution of N$^δ$,N$^ω$-bis((benzyloxy)carbonyl)-N2-(tert-butoxycarbonyl)-L-arginine (7.87 g, 14.5 mmol) and benzyl alcohol (2.28 mL, 22 mmol) in anhydrous DCM (125 mL) under nitrogen was treated with DCC (3.30 g, 16 mmol) and DMAP (0.20 g, 1.64 mmol) and slowly allowed to reach room temperature and stirred overnight (20 h). The solution/suspension was filtered and the solid rinsed with DCM. The filtrate was added directly to a column of silica gel (~300 cc) and eluted with 3% ethyl acetate/DCM to afford 9.01 g (98%) as a white solid. NMR (CDCl$_3$): δ 9.42 (br s, 1H), 9.22 (br s, 1H), 7.38-7.24 (m, 15H), 5.18 (s, 2H), 5.13-5.07 (m, 5H), 4.32-4.28 (m, 1H), 3.94 (t, 2H, J=8 Hz), 1.78-1.59 (m, 4H), 1.39 (s, 9H)

h. benzyl Nd,Nw-bis((benzyloxy)carbonyl)-L-argininate

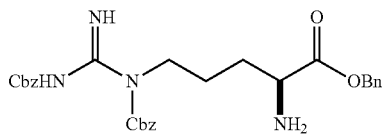

A solution of benzyl N$^δ$,Nω-bis((benzyloxy)carbonyl)-N2-(tert-butoxycarbonyl)-L-argininate (8.86 g, 14 mmol) in 1:1 TFA/DCM (50 mL) was gently warmed to induce bubbling, then stirred at room temperature for 1 h. The mixture was concentrated in vacuo (exhaustively to remove all TFA possible) and the residual oil dissolved in 1:1 DCM/MeOH and stirred for 15 min with DOWEX 550A-upw resin (~50 g) in order to neutralize the salt. The mixture was filtered, resin washed with 1:1 DCM/MeOH, and the filtrate concentrated in vacuo to afford 6.64 g (89%) of benzyl N$^δ$,N$^ω$-bis((benzyloxy)carbonyl)-L-argininate which was carried forward without further purification.

i. L-arginyl-L-arginine

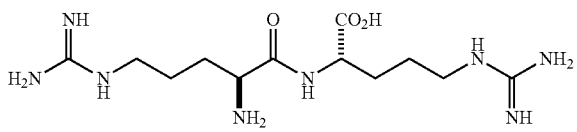 [SMILES: N=C(N)NCCC[C@H](NC(=O)[C@@H](N)CCCNC(=N)N)C(=O)O]

A stirred solution/suspension of benzyl N$^δ$,N$^ω$-bis((benzyloxy)carbonyl)-N2-(N2,Nd,Nw-tris((benzyloxy)carbonyl)-L-arginyl)-L-argininate (2.182 g, 2.0 mmol) in methanol (30 mL) and ethyl acetate (15 mL) under nitrogen was treated with 10% Pd/C (0.15 g), then evacuated and purged several times with hydrogen via balloon. The mixture was heated to 45° C. and stirred for 24 h under hydrogen, then the flask cooled and evacuated with nitrogen and carefully filtered through Celite with water rinse. The filtrate was concentrated in vacuo to afford 0.66 g (100%) as a white foam. NMR (D$_2$O): δ 3.98 (dd, 1H, J=5 Hz, 8 Hz), 3.84 and 3.23 (1H, both m, rotamers) 3.01-2.97 (m, 4H), 1.65-1.38 (m, 8H).

Compound 1: (L,L) Lysyl-lysine EPA Salt (mono)

A stirred solution of (L,L)-lysyllisine (0.87 g, 3.16 mmol) in 15 mL of methanol was heated to 45° C., then treated with a combined solution of EPA (1.0 g, 3.32 mmol) and alpha-D-tocopherol (36 mg pre-dissolved in 0.5 mL of ethyl acetate and added to the EPA solution) in methanol (15 mL). The reaction cooled over 15 min and the solvent was concentrated in vacuo to a foam. The foam was triturated from cold acetonitrile, collected and dried to afford 1.56 g (86%) as a light pink solid. MP 92-94° C. NMR (d$_4$-MeOH): δ 5.25-5.42 (m, 10H), 4.23 (dd, 1H, J=5 Hz, 8 Hz), 3.40 (t, 1H, J=6.5 Hz), 2.78-2.91 (m, 12H), 2.16 (t, 2H, J=8 Hz), 2.03-2.12 (m, 4H), 1.89-1.80 (m, 1H), 1.73-1.58 (m, 9H), 1.50-1.40 (m, 4H), 0.95 (t, 3H, J=8 Hz). $^{13}$C NMR (151 MHz, cd$_3$od) δ 181.05, 177.35, 173.99, 131.36, 129.42, 128.02, 128.00, 127.76, 127.73, 127.55, 127.50, 126.76, 54.32, 54.02, 47.16, 39.09, 38.98, 37.12, 33.73, 31.75, 26.84, 26.83, 26.81, 26.27, 25.15, 25.13, 25.12, 25.01, 22.33, 21.80, 20.09, 13.26.

Compound 2: (L,L) Lysyl-lysine bis-EPA Salt

A stirred solution of (L,L)-lysyllysine (549 mg, 2.0 mmol) in methanol (10 mL) under nitrogen was heated to 45° C., then treated with a combined solution of EPA (1.39 g, 4.6 mmol) and alpha-D-tocopherol (50 mg pre-dissolved in 0.5 mL of ethyl acetate and added to the EPA solution) in methanol (10 mL). The reaction cooled over 15 min and the solvent was concentrated in vacuo to a foam. The foam was triturated from cold acetonitrile, collected and dried to afford 1.60 g (89%) as a very pale peach solid. MP 85-87° C. NMR (d$_4$-MeOH): δ 5.25-5.45 (m, 20H), 4.23 (dd, 1H, J=5 Hz, 8 Hz), 3.64 (t, 1H, J=6.5 Hz), 2.75-2.95 (m, 20H), 2.19 (t, 4H, J=8 Hz), 2.00-2.15 (m, 8H), 1.80-1.90 (m, 1H), 1.70-1.80 (m, 2H), 1.60-1.70 (m, 9H), 1.40-1.55 (m, 4H), 0.95 (t, 6H, J=8 Hz). $^{13}$C NMR (151 MHz, cd$_3$od) δ 179.49, 177.16, 171.11, 131.36, 129.18, 128.02, 127.97, 127.94, 127.74, 127.71, 127.59, 127.50, 126.76, 54.50, 53.25, 39.02, 38.81, 35.83, 32.11, 31.58, 26.66, 26.62, 26.58, 25.75, 25.15, 25.13, 25.12, 25.02, 22.37, 21.29, 20.09, 13.27.

Compound 3: (L,L) Lysyl-lysine DHA Salt (mono)

A stirred solution of (L,L)-lysyllisine (0.87 g, 3.17 mmol) in methanol (13 mL) was heated to 45° C., then treated with a combined solution of DHA (1.09 g, 3.32 mmol) and alpha-D-tocopherol (38 mg pre-dissolved in 0.5 mL of ethyl acetate and added to the DHA solution)

in methanol (13 mL). The reaction cooled over 15 minutes and was filtered through Celite. The filtrate was concentrated in vacuo to a foam. The foam was triturated from cold acetonitrile, collected and dried to afford 1.85 g (97%) as a white solid. MP 89-91° C. NMR (d$_4$-MeOH): δ 5.25-5.44 (m,12 H), 4.23 (dd, 1H, J=5 Hz, 8 Hz), 3.41 (t, 1H, J=6.5 Hz), 2.78-2.91 (m, 14H), 2.32-2.37 (m, 2H) 2.16-2.20 (m, 2H), 2.03-2.10 (m, 2H), 1.89-1.80 (m, 1H), 1.74-1.58 (m, 7H), 1.48-1.40 (m, 4H), 0.95 (t, 3H, J=7.5 Hz). $^{13}$C NMR (151 MHz, CD$_3$OD) δ 180.57, 177.35, 131.36, 129.20, 128.04, 128.02, 127.78, 127.76, 127.72, 127.69, 127.66, 127.59, 127.50, 126.76, 54.32, 53.97, 47.30, 47.16, 39.08, 38.97, 37.33, 33.64, 31.73, 26.81, 26.78, 25.15, 25.14, 25.11, 25.02, 23.99, 22.32, 21.77, 20.09, 13.27.

Compound 4: (L,L) Lysyl-lysine bis DHA Salt

A stirred solution of (L,L)-lysyllisine (0.55 g, 2.0 mmol) in methanol (15 mL) was heated to 45° C., then treated with a combined solution of DHA (1.51 g, 4.6 mmol) and alpha-D-tocopherol (50 mg pre-dissolved in 0.5 mL of ethyl acetate and added to the DHA solution) in methanol (15 mL). The reaction cooled over 15 minutes and was filtered through Celite. The filtrate was concentrated in vacuo to a foam. The foam was triturated from cold acetonitrile, collected and dried to afford 1.68 g (87%) as a white solid. MP 64-67° C. NMR (d$_4$-MeOH): δ 5.25-5.43 (m, 24H), 4.23 (dd, 1H, J=5 Hz, 8 Hz), 3.64 (t, 1H, J=6.5 Hz), 2.78-2.92 (m, 24H), 2.32-2.38(m, 4H), 2.24-2.20 (m, 4H), 2.01-2.10 (m, 4H), 1.62-1.87 (m, 8H), 1.41-1.53 (m, 4H), 0.95 (t, 6H, J=7.5 Hz). $^{13}$C NMR (151 MHz, cd$_3$od) δ 179.00, 177.15, 171.03, 131.36, 128.78, 128.02, 127.98, 127.95, 127.76, 127.73, 127.68, 127.63, 127.50, 126.76, 54.49, 53.24, 47.30, 47.16, 39.02, 38.80, 36.22, 32.07, 31.57, 26.65, 26.58, 25.15, 25.14, 25.11, 25.02, 23.54, 22.36, 21.26, 20.09, Compound 5:(L,L) Lysyl-lysine EPA DHA Salt A stirred solution of (L,L)-lysyllisine (0.53 g, 1.93 mmol) in 15 mL of methanol was heated to 45° C., then treated with a combined solution of EPA (0.60 g, 1.97 mmol) and DHA (0.65 g, 1.97 mmol) in 15 mL of methanol. The reaction cooled over 15 minutes and was filtered through Celite. The filtrate was concentrated in vacuo to give an off-white foam. The foam was triturated from cold acetonitrile, collected and dried to afford 1.56 g (89%) as a beige solid. MP 76-78° C. NMR (d$_4$-MeOH): δ 5.25-5.43 (m, 22H), 4.23 (dd, 1H, J=5 Hz, 8 Hz), 3.60 (t, 1H, J=6.5 Hz), 2.78-2.92 (m, 22H), 2.32-2.37 (m, 2H), 2.18-2.23 (m, 4H), 2.03-2.12 (m, 6H), 1.60-1.88 (m, 10H), 1.41-1.52 (m, 4H), 0.95 (t, 6H, J=7.5 Hz). $^{13}$C NMR (151 MHz, cd$_3$od) δ 179.58, 179.23, 177.17, 171.18, 131.36, 129.19, 128.85, 128.02, 127.96, 127.95, 127.93, 127.76, 127.74, 127.73, 127.71, 127.68, 127.62, 127.59, 127.50, 126.76, 54.50, 53.27, 47.59, 47.45, 47.30, 47.16, 39.03, 38.81, 36.42, 35.87, 32.15, 31.58, 26.67, 26.63, 26.59, 25.76, 25.15, 25.14, 25.12, 25.11, 25.02, 23.62, 22.37, 21.30, 20.09, 13.27.

Compound 6:(L,L) Lysyl-lysine bis Gabapentin Salt

A stirred solution of (L,L)-lysyllisine (0.154 g, 0.56 mmol) in 8 mL of methanol was heated to 45° C., then gabapentin (0.20 g, 1.18 mmol) was added. The reaction cooled over 15 minutes and was filtered through Celite. The filtrate was concentrated in vacuo to give a foam. The foam was triturated from cold acetonitrile, collected and dried to afford 0.30 g (92%) as a white solid. MP 132-134° C. NMR (D$_2$O): δ 4.01 (dd, 1H, J=5 Hz, 8 Hz), 3.24 (t, 1H, J=6.5), 2.78-2.74 (m, 8H), 2.22 (s, 4H), 1.67-1.43 (m, 8H), 1.31-1.17 (m, 24H).

Compound 7: (L,L) Lysyl-lysine EPA Niacin Salt

A stirred solution of (L,L)-lysyllisine (0.12 g, 0.44 mmol) in 5 mL of methanol was heated to 45° C., then Niacin (0.05 g, 0.44 mmol) was added. After 10 minutes a combined solution of EPA (0.39 g, 1.31 mmol) and alpha-D-tocopherol (6 mg pre-dissolved in 0.5 mL of ethyl acetate and added to the EPA solution) in 5 mL of methanol was added. The reaction cooled over 15 minutes and the solvent was concentrated in vacuo to give a foam. The foam was triturated from cold acetonitrile, collected and dried to afford 0.25 g (82%) as an off-white solid. MP 116-119° C. NMR (d$_4$-MeOH): δ 9.04 (s, 1H), 8.53 (dd, 1H, J=2 Hz, 5 Hz), 8.30 (dt, 1H, J=2 Hz, 8 Hz), 7.43 (dd, 1H, J=5 Hz, 8 Hz), 5.41-5.25 (m, 10H), 4.24 (dd, 1H, J=5 Hz, 8 Hz), 3.75 (t, 1H, J=6.5 Hz), 2.94-2.78 (m, 12H), 2.22 (t, 2H, J=7.5 Hz), 2.13-2.07 (m, 4H), 1.89-1.79 (m, 4H), 1.73-1.60 (m, 6H), 1.59-1.43 (m, 4H), 0.95 (t, 3H, J=7.5 Hz)

Compound 8: (L,L) Lysyl-lysine EPA Ibuprofen Salt

A solution of (L,L)-lysyllisine (0.15 g, 0.56 mmol) in 5 mL of methanol was treated with Ibuprofen (0.12 g, 0.56 mmol) and stirred for 5 minutes. The solvent was concentrated in vacuo to give a foam. The foam was triturated in acetonitrile and the solvent decanted and replaced with 5 mL of methanol. The solution was heated to 45° C., then treated with a combined solution of EPA (0.20 g, 0.67 mmol) and alpha-D-tocopherol (15 mg pre-dissolved in 0.5 mL of ethyl acetate and added to the EPA solution) in 3 mL of methanol. The reaction cooled over 15 minutes and the solvent was concentrated in vacuo to give a foam. The foam was triturated from cold acetonitrile, collected and dried to afford 0.31 g (70%) as a beige solid. MP 89-92° C. NMR (d$_4$-MeOH): δ 7.22 (d, 2H, J=6 Hz), 7.03 (d, 2H, J=6 Hz), 5.41-5.25 (m, 10H), 4.23 (dd, 1H, J=5 Hz, 8 Hz), 3.62 (t, 1H, J=6.5 Hz), 3.54 (dd, 1H, J=7 Hz, 14 Hz), 2.90-2.78 (m, 12H), 2.41 (d, 2H, J=7 Hz), 2.20 (t, 2H, J=7.5 Hz), 2.13-2.05 (m, 4H), 1.89-1.58 (m, 11H), 1.51-1.42 (m, 4H), 1.38 (d, 3H, J=7 Hz), 0.95 (t, 3H, J=7.5 Hz), 0.86 (d, 6H, J=6.5 Hz)

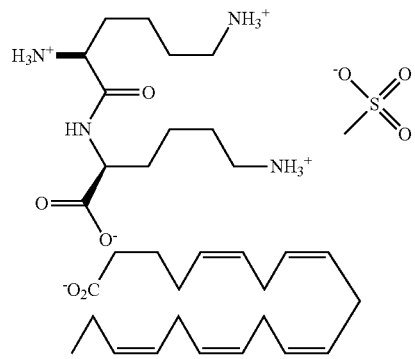

Compound 9: (L,L) Lysyl-lysine EPA methanesulfonic acid salt

A stirred solution of (L,L)-lysyllisine (0.09 g, 0.33 mmol) in 5 mL of methanol was heated to 45° C., then methanesulfonic acid (0.03 g, 0.33 mmol) was added. After 10 minutes a combined solution of EPA (0.297 g, 0.98 mmol) and alpha-D-tocopherol (65 mg pre-dissolved in 0.5 mL of ethyl acetate and added to the EPA solution) in 5 mL of methanol was added. The reaction cooled over 15 minutes and was filtered through Celite. The filtrate was concentrated in vacuo to give a foam. The foam was triturated from cold acetonitrile, collected and dried to afford 0.19 g (84%) as a beige solid. NMR (d$_4$-MeOH): δ 5.41-5.25 (m, 10H), 4.23 (dd, 1H, J=5 Hz, 8 Hz), 3.68 (t, 1H, J=6.5 Hz), 2.95-2.88 (m, 4H), 2.85-2.79 (m, 8H), 2.69 (s, 3H), 2.20 (t, 2H, J=7.5 Hz), 2.11-2.03 (m, 4H), 1.90-1.73 (m, 4H), 1.71-1.60 (m, 6H), 1.54-1.42 (m, 4H), 0.95 (t, 3H, J=7.5 Hz).

Compound 10: (L,L) arginyl-lysine bis Gabapentin Salt

A stirred mixture of (L,L)-arginyllysine (151 mg, 0.5 mmol) and gabapentin (180 mg, 1.05 mmol) in 2:1 methanol/water (6 mL) was heated to 45° C. The reaction cooled over 15 minutes and was concentrated in vacuo to a foam. The foam was triturated from cold acetonitrile, collected and dried to afford 294 mg (91%) as a white solid. NMR (DMSO): δ 3.92 (dd, 1H, J=5 Hz, 8 Hz), 3.21-3.15 (m, 1H) 3.01-2.95 (m, 2H), 2.67 (s, 4H), 2.58 (t, 2H, J=7 Hz), 2.17 (s, 4H), 1.92 (s, 2H), 1.61-1.10 (m, 28H).

Compound 11: (L,L) arginyl-arginine bis Gabapentin Salt

A stirred mixture of L-arginyl-L-arginine (330 mg, 1.0 mmol) and gabapentin (360 mg, 2.1 mmol) in 2:1 methanol/water (12 mL) was heated to 45° C. The reaction cooled for 15 minutes and was filtered through Celite. The filtrate was concentrated in vacuo to a foam. The foam was triturated from cold acetonitrile, collected and dried to afford 602 mg (87%) as a white solid. NMR (D2O): δ 4.00 (dd, 1H, J=5 Hz, 8 Hz), 3.26-3.23 (m, 1H), 3.03-2.98 (m. 4H), 2.74 (s, 4H), 2.19 (s, 4H), 1.56-1.14 (m, 28H).

Stability

Stability analysis was performed using 1H NMR (400 MHz) with acetic acid-d4 at various time point (typically days 1, 14, 30 and 60) using samples exposed to air and light at ambient temperature (clear vials with no caps). Semi-quantitative analysis based on integration and resolution of the vinyl peaks (2.75-3.00 ppm) was used to categorize samples as 1=>95%, 2=75-95%, 3=50-75%, 4=<50%, where the percent value indicate the amount of sample remaining relative to the original sample at day 1.

TABLE 3

Stability[1] of representative compounds compared to EPA ethyl ester

| Compound | Day 3 | Day 14 | Day 30 | Day 60 |
|---|---|---|---|---|
| EPA ethyl ester | 1 | 1-2 | 4 | 4 |
| Lysyl-lysine EPA | 1 | 1 | 1 | 1 |
| Lysyl-lysine Bis-EPA | 1 | 1 | 1 | 1 |
| Arginyl-arginine Bis-EPA | 1 | 1 | 1 | 1 |
| Arginyl-lysine Bis-EPA | 1 | 1 | 1 | 1 |
| Lysyl-lysine DHA | 1 | 1 | 1 | 1 |
| Lysyl-lysine Bis DHA | 1 | 1 | 1 | 1 |
| Arginyl-arginine Bis-DHA | 1 | 1 | 1 | 1 |
| Arginyl-lysine Bis-DHA | 1 | 1 | 1 | 1 |
| Lysyl-lysine EPA Nicotinic Acid | 1 | 1 | 1 | 1 |
| Lysyl-lysine EPA Ibuprofen | 1 | 1 | 1 | 1 |

[1]Stability by NMR of compounds exposed to air for the indicated time: 1 = >95%, 2 = 75-95%, 3 = 50-75%, 4 = <50%.

Pharmacokinetic Properties

Experiments via Oral Gavage: Oral pharmacokinetic parameters of TP-212 (Lysyl-Lysine Bis-EPA), TP-312 (Lysyl-Lysine Bis-DHA), EPA-EE, EPA FFA and DHA FFA were determined in Sprague-Dawley rats. EPA-EE is 97% pure ethyl ester form of eicosapentaenoic acid. It is the principal polyunsaturated fatty acid in Vascepa, an Omega-3 compound approved in the U.S. for the treatment of severe hypertriglyceridemia. EPA FFA is 97% pure free fatty acid form of eicosapentaenoic acid and DHA FFA is 98% pure free fatty acid DHA. EPA FFA and DHA FFA are the two principal poly-unsaturated fatty acids in Epanova, an Omega-3 compound approved in the U.S. for the treatment of severe hypertriglyceridemia. The subject drugs were administered by oral gavage as an aqueous solution in de-ionized water to 6 Sprague-Dawley rats per group (3 males and 3 females). Rats were dosed at 40 mg/kg. Blood samples were obtained from each rat by jugular vein catheter. Samples were collected at pre-dose and at 0.25, 0.5, 1, 2, 4, 8, 12 and 18 hours post dose. Blood samples were centrifuged to separate red blood cells and the resulting plasma samples were analyzed for free EPA or free DHA. Free EPA or free EPA was extracted from rat plasma with hexane at acidic condition without hydrolysis. Detection was by MS-MS monitoring of negative ion for EPA or DHA. Calculated pharmacokinetic values are mean values from 6 rats for each study drug.

Experiments via Intravenous Injection: TP-212 and TP-312 were administered by intravenous injection (20 mg/kg) to Sprague-Dawley rats (n=6/group—3 male and 3 female), and plasma was obtained from serial blood samples taken from each animal at scheduled times (Predose, 0.25, 0.5, 1, 2, and 4 hours post dose). Blood samples were centrifuged to separate red blood cells and the resulting plasma samples were analyzed for free EPA or free DHA. Free EPA or free DHA was extracted from rat plasma with hexane at acidic condition without hydrolysis. Detection was by MS-MS monitoring of negative ion for EPA or DHA. Calculated pharmacokinetic values are mean values from 6 rats for each study drug.

For all figures and tables, the data are adjusted as follows for comparative purposes. First, the actual plasma levels are baseline adjusted. Thus, for each study arm, the pre-dose level (time=0) is subtracted from the actual plasma levels at each time point, with negative values adjusted to zero. Second, these baseline adjusted values are further adjusted to be molar dose equivalent on a comparative basis among the study arms with respect to EPA or DHA payload (i.e., as if equal amounts of free fatty acid EPA or DHA are administered in each study arm).

Results

FIG. 1 and Table 4 show the plasma levels of free EPA of TP-212 compared to EPA-EE and EPA-FFA, all administered via oral gavage. The data indicate that the Cmax of TP-212 is approximately 8.9 and 7.4 times greater than EPA-EE and EPA-FFA, respectively; and the AUC over 18 hours (ug*h/mL) of TP-212 is approximately 2.6 and 1.8 times greater than EPA-EE and EPA-FFA, respectively.

TABLE 4

Plasma levels of free EPA of TP-212 (oral).

| | ug/mL * | | |
|---|---|---|---|
| Hour | TP-212 | EPA-EE | EPA-FFA |
| 0 | 0.0 | 0.0 | 0.0 |
| 0.25 | 0.3 | 0.3 | 0.0 |
| 0.5 | 9.5 | 0.5 | 1.3 |
| 1 | 3.9 | 0.7 | 0.5 |
| 2 | 3.2 | 0.8 | 0.8 |
| 4 | 1.5 | 1.1 | 1.1 |
| 8 | 0.6 | 0.5 | 0.9 |
| 12 | 0.0 | 0.0 | 0.3 |
| 18 | 0.0 | 0.0 | 0.0 |
| Tmax | 30 min | 4 hrs | 30 min |
| Cmax (ug/mL) | 9.5 | 1.1 | 1.3 |
| AUC [0-18 hrs (ug*h/mL)] | 18.3 | 7.2 | 10.5 |

* Molar dose equivalent, baseline adjusted.

Figure 2:
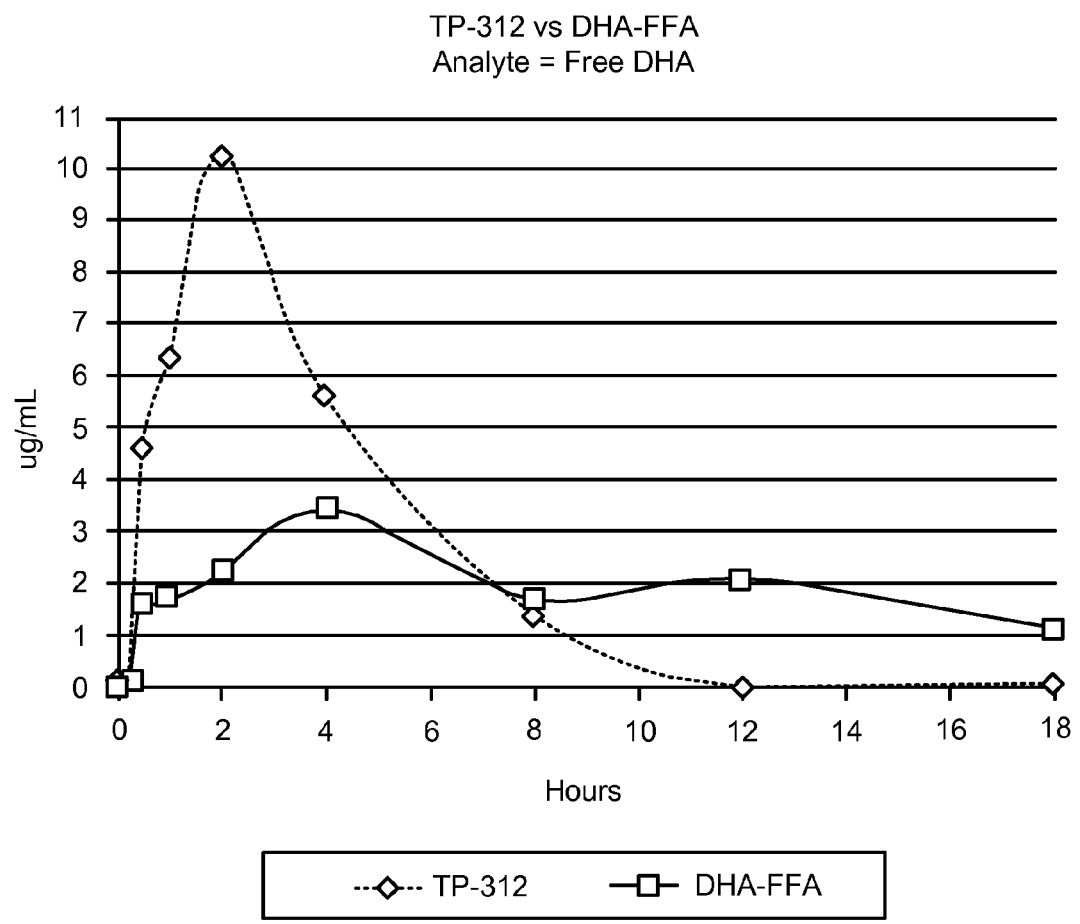
FIG. 2: plasma levels of free DHA of TP-312 compared to DHA FFA, all administered via oral gavage.

FIG. 2 and Table 5 show the plasma levels of free DHA of TP-312 compared to DHA FFA, all administered via oral gavage. The data indicate that the Cmax of TP-312 is approximately 3.0 times greater than DHA-FFA; and the AUC over 18 hours (ug*h/mL) of TP-312 is approximately 1.2 times greater than DHA-FFA.

TABLE 5

Plasma levels of free DHA of TP-312 (oral).

| Hour | ug/mL * | |
|---|---|---|
| | TP-312 | DHA-FFA |
| 0 | 0.0 | 0.0 |
| 0.25 | 0.0 | 0.0 |
| 0.5 | 4.6 | 1.8 |
| 1 | 6.3 | 1.8 |
| 2 | 10.4 | 2.2 |
| 4 | 5.6 | 3.4 |
| 8 | 1.4 | 1.7 |
| 12 | 0.0 | 2.1 |
| 18 | 0.0 | 1.2 |
| Tmax | 2 hrs | 4 hrs |
| Cmax (ug/mL) | 10.4 | 3.4 |
| AUC [0-18 hrs (ug*h/mL)] | 44.4 | 36.3 |

* Molar Dose Equivalent, Baseline Adjusted

Figure 3:
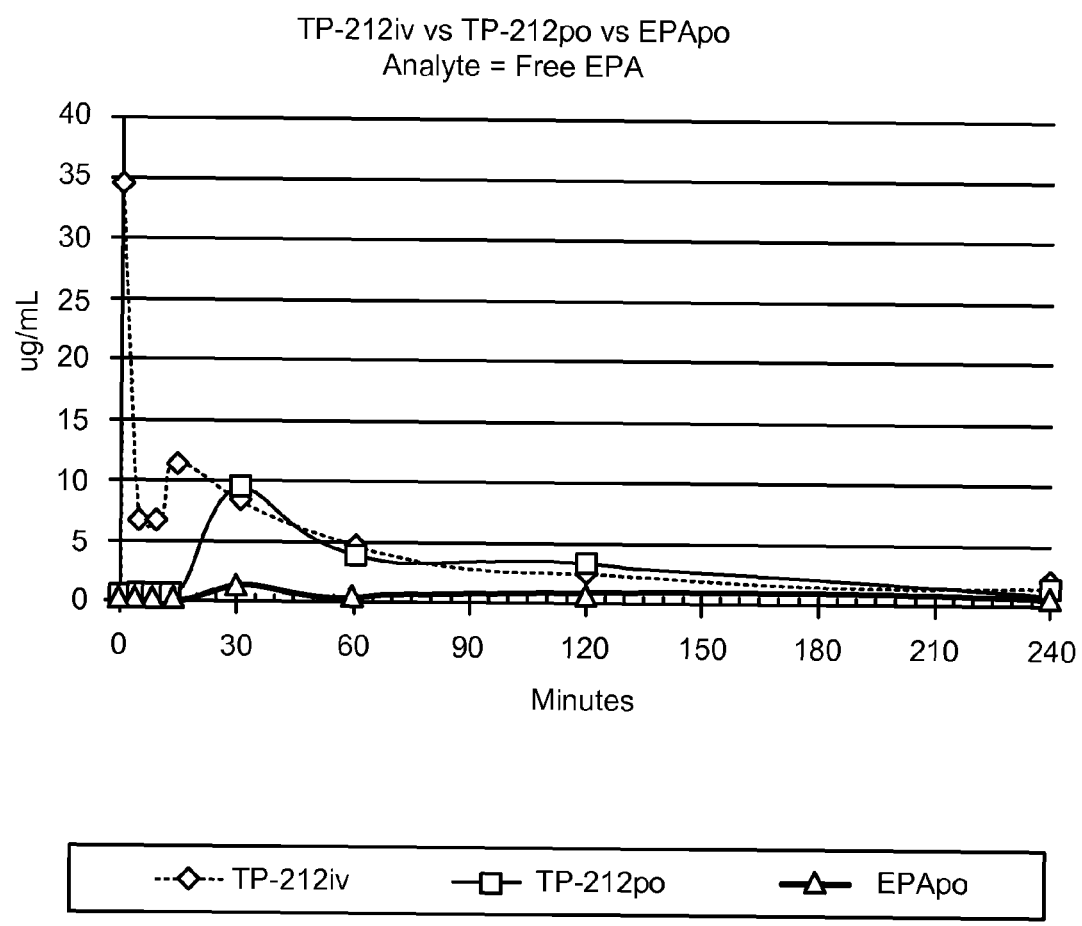
FIG. 3: plasma levels of free EPA of TP-212 administered via intravenous injection (TP-212iv) versus TP-212 administered via oral gavage (TP-212po) versus EPA-FFA administered via oral gavage (EPApo).

FIG. 3 and Table 6 show the plasma levels of free EPA of TP-212 administered via intravenous injection (TP-212iv) versus TP-212 administered via oral gavage (TP-212po) versus EPA-FFA administered via oral gavage (EPApo). The data indicate that the Cmax of TP-212iv is approximately 3.6 and 27 times greater than TP-212po and EPA-FFApo, respectively; the AUC over 1 hour of TP-212iv is approximately 1.8 and 13.4 times greater than TP-212po and EPApo, respectively; and the AUC over 4 hours of TP-212iv is approximately 1.2 and 5.1 times greater than TP-212po and EPApo, respectively.

TABLE 6

Plasma levels of free EPA of TP-212 (iv)

| Min | ug/mL * | | |
|---|---|---|---|
| | TP-212iv | TP-212po | EPApo |
| 0 | 0.0 | 0.0 | 0.0 |
| 1 | 34.5 | ** | ** |
| 5 | 6.6 | ** | ** |
| 10 | 6.4 | ** | ** |
| 15 | 11.4 | 0.3 | 0.0 |
| 30 | 8.8 | 9.5 | 1.3 |
| 60 | 4.6 | 3.9 | 0.5 |
| 120 | 2.3 | 3.2 | 0.8 |
| 240 | 1.8 | 1.5 | 1.1 |
| Tmax | 1 min | 30 min | 30 min |
| Cmax (ug/mL) | 34.5 | 9.5 | 1.3 |
| AUC [0-1 hrs (ug*h/mL)] | 8.3 | 4.6 | 0.6 |
| AUC [0-4 hrs (ug*h/mL)] | 15.9 | 12.8 | 3.1 |

Figure 4:
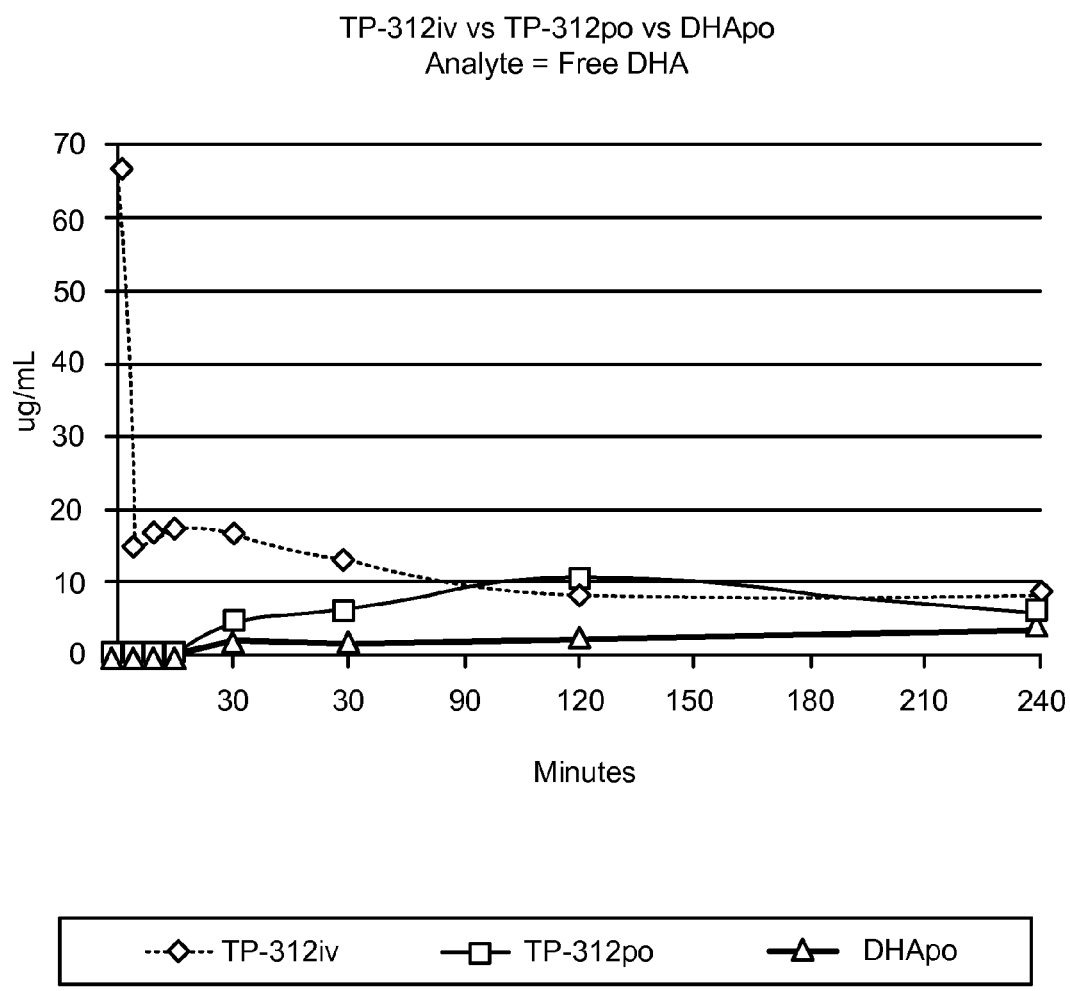
FIG. 4: plasma levels of free DHA of TP-312 administered via intravenous injection (TP-312iv) versus TP-312 administered via oral gavage (TP-312po) versus DHA-FFA administered via oral gavage (DHApo).
Figure 5A:
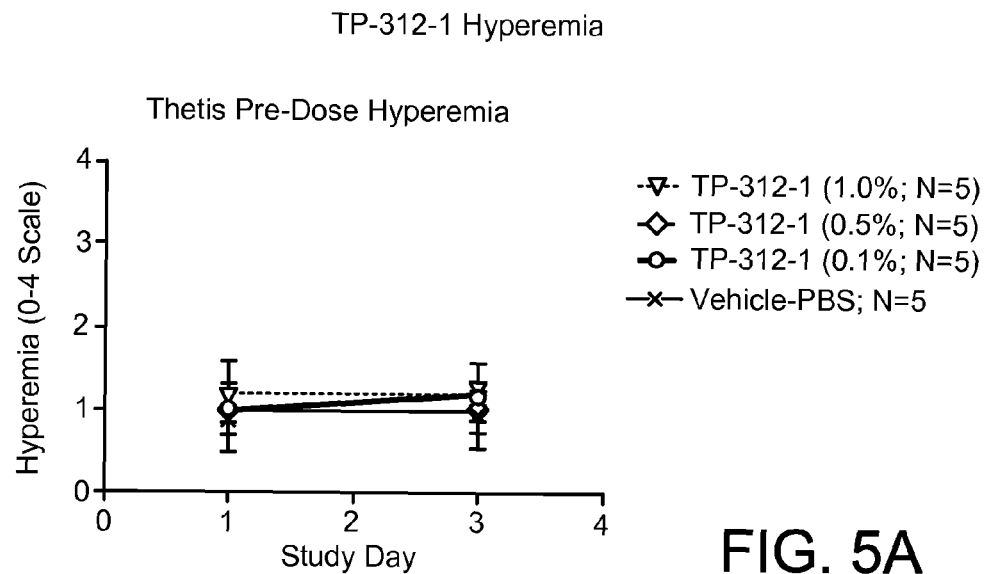
FIG. 5A-C: TP-312-1 Hyperemia (A) Pre-dose, (B) Post-dose, (C) delta.
Figure 5B:
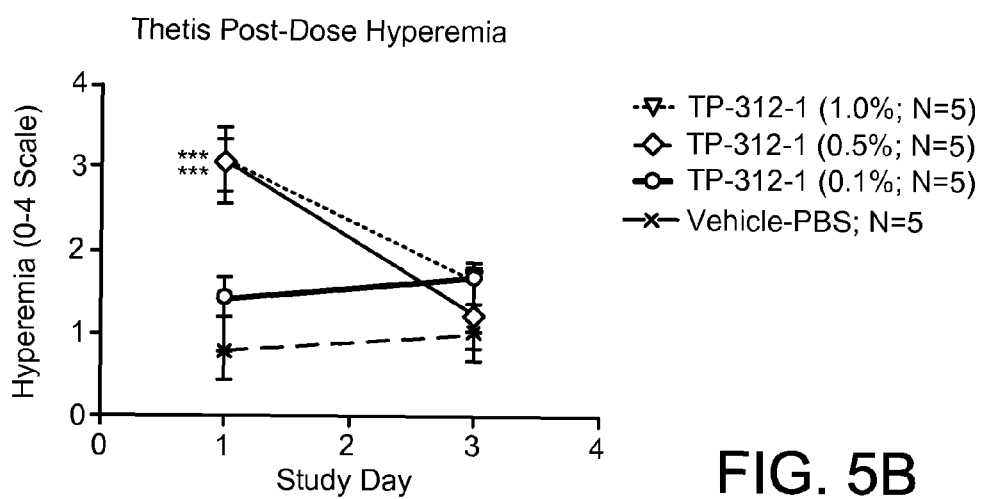
Figure 5C:
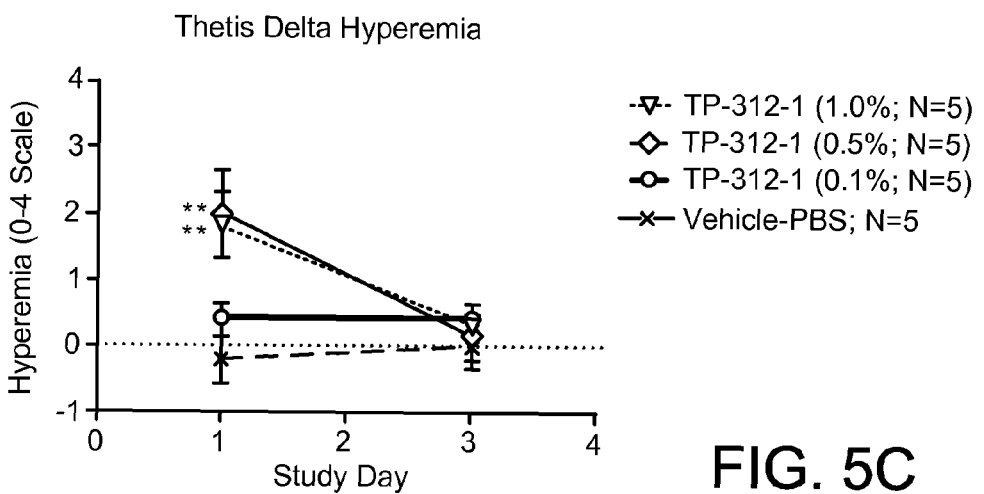
Figure 6A:
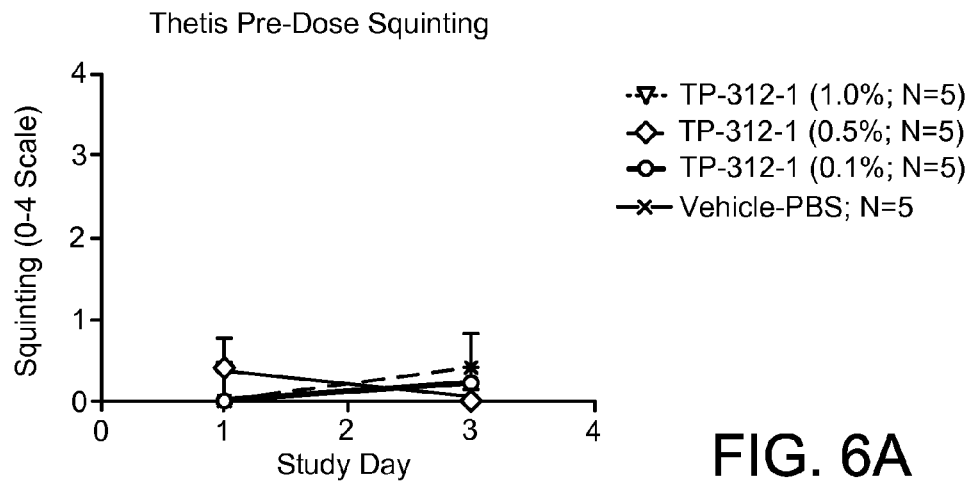
FIG. 6A-C: TP-312-1 Squinting (A) Pre-dose, (B) Post-dose, (C) delta.
Figure 6B:
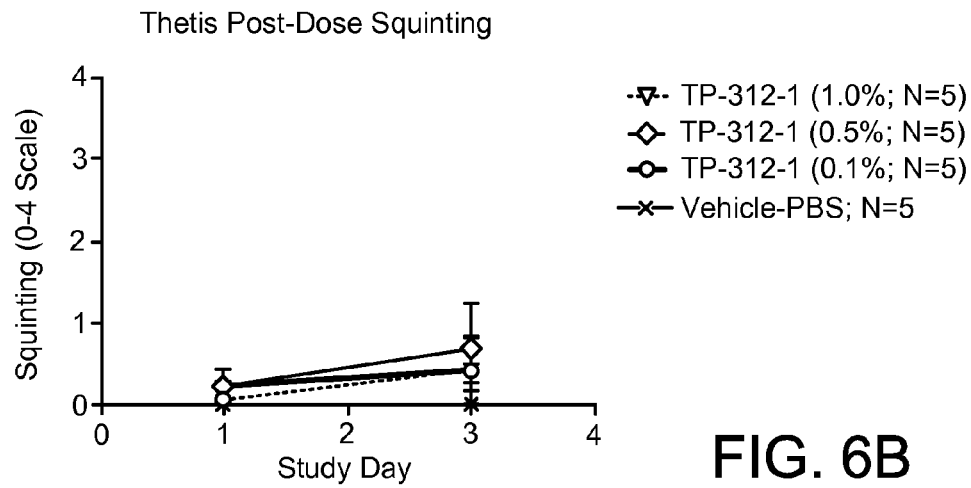
Figure 6C:
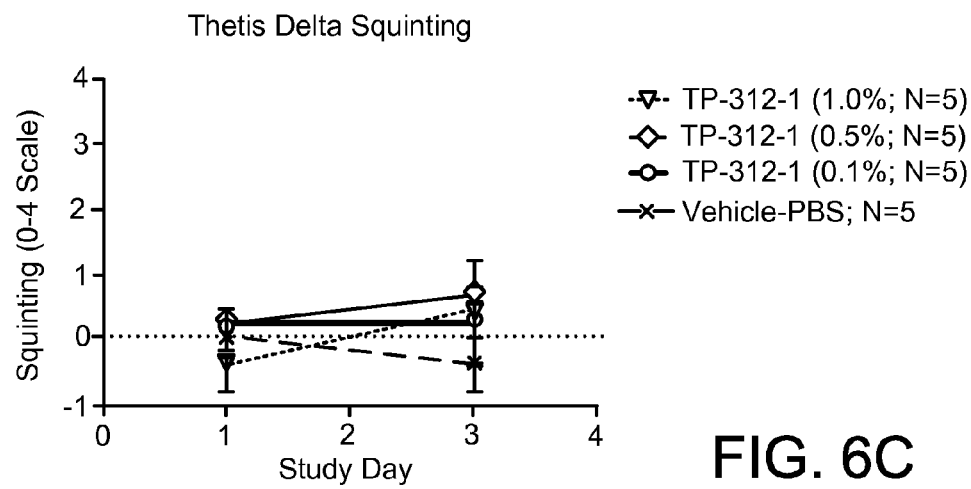
Figure 7A:
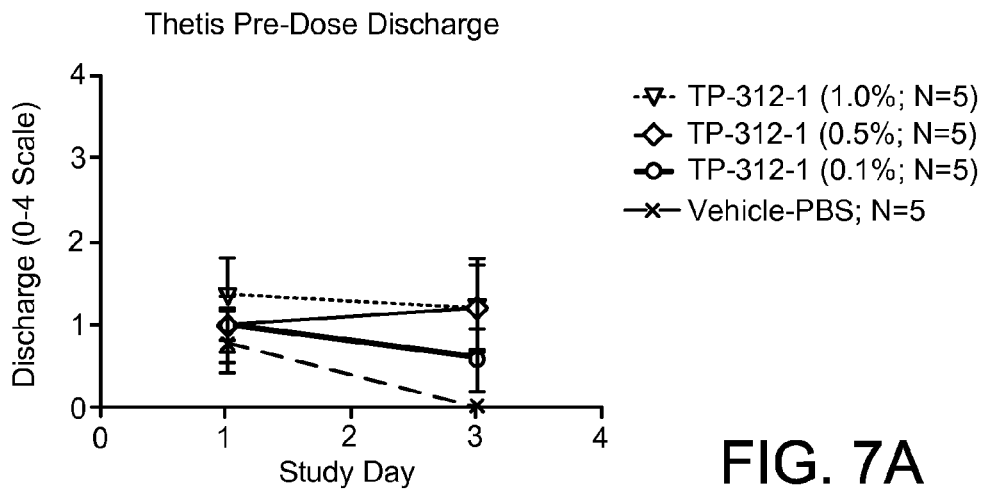
FIG. 7A-C: TP-312-1 Discharge (A) Pre-dose, (B) Post-dose, (C) delta.
Figure 7B:
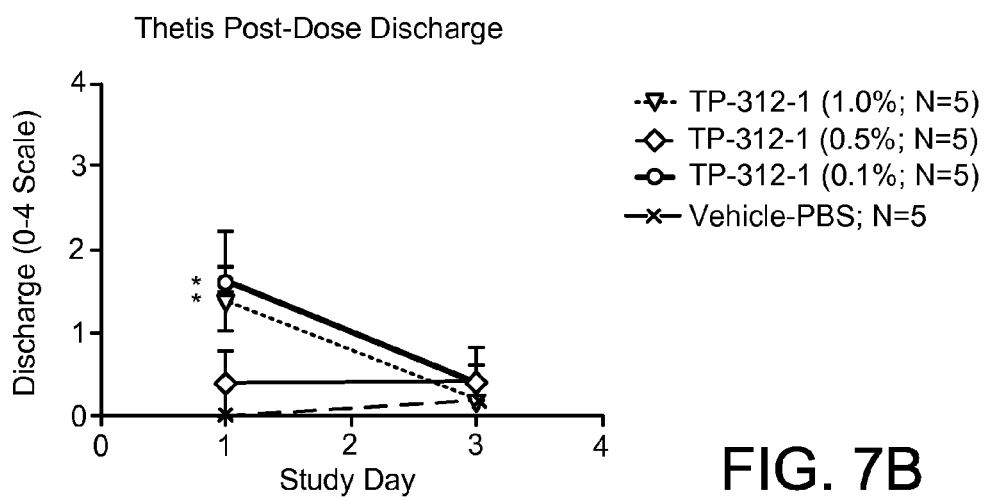
Figure 7C:
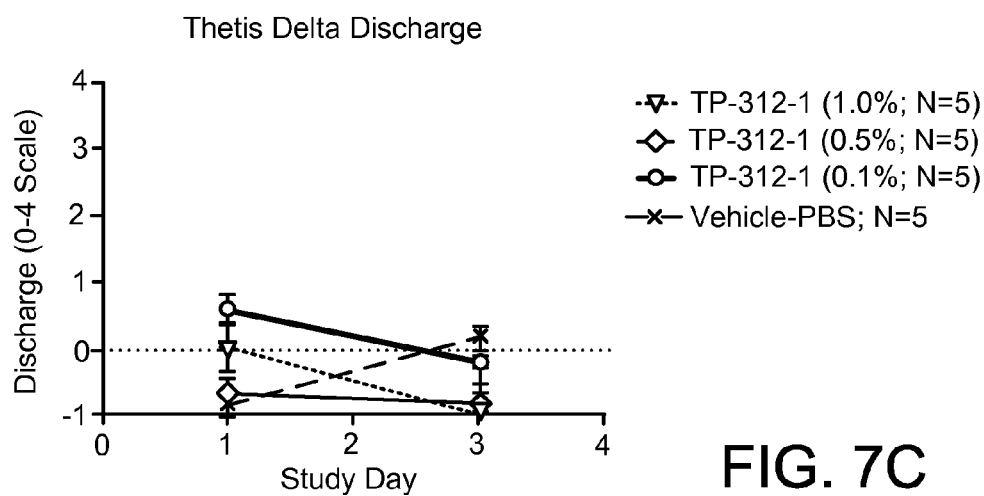
Figure 8A:
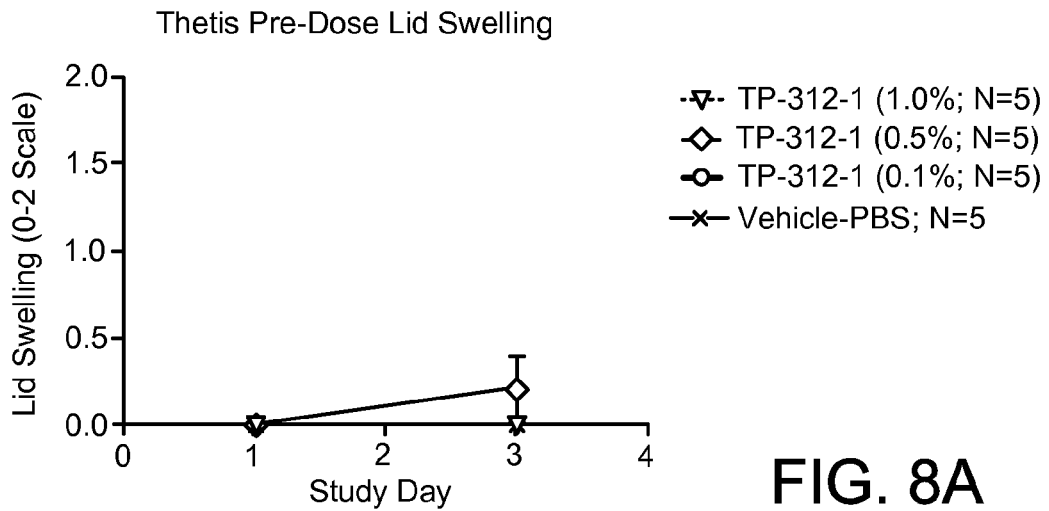
FIG. 8A-C: TP-312-1 Lid Swelling (A) Pre-dose, (B) Post-dose, (C) delta.
Figure 8B:
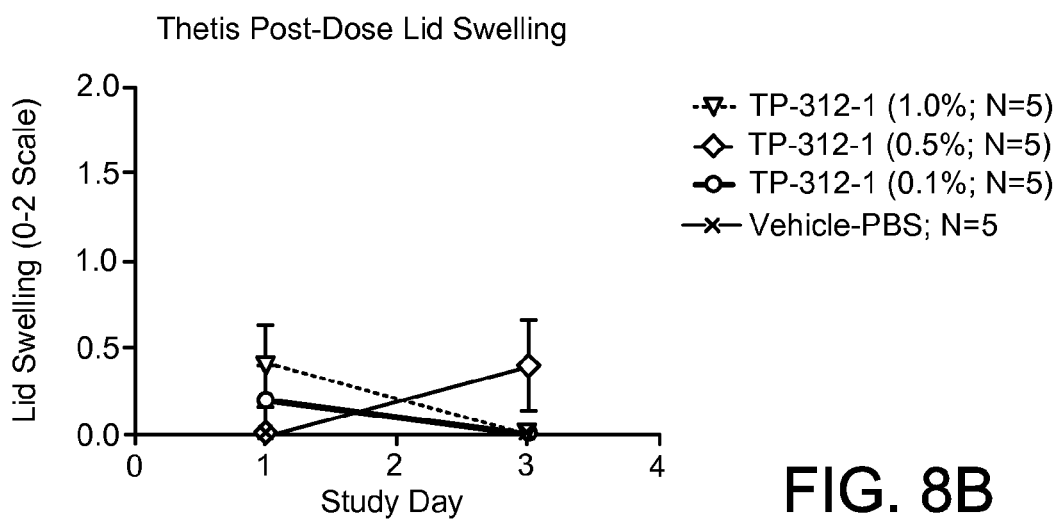
Figure 8C:
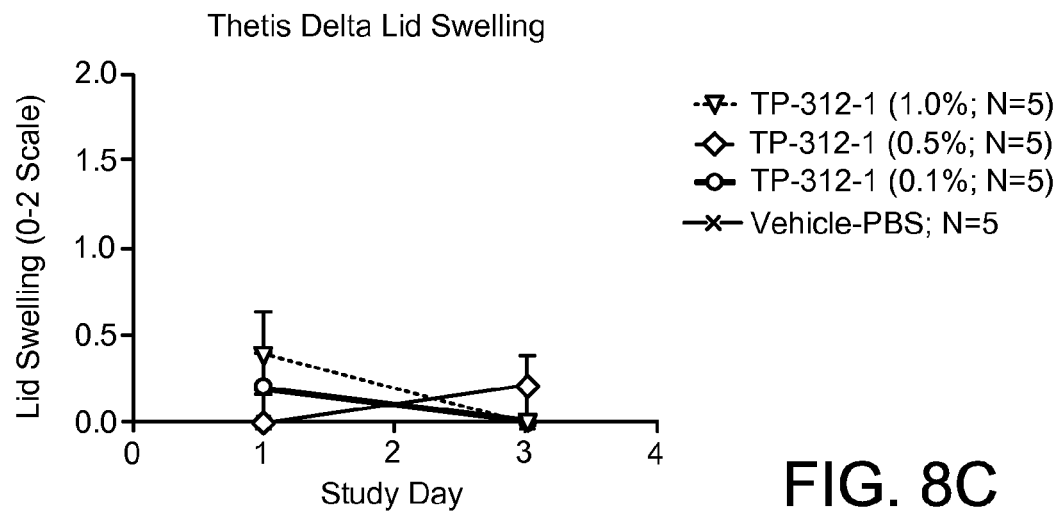

* Molar dose equivalent, baseline adjusted
** No blood samples on studies with oral doses FIG. 4 and Table 7 show the plasma levels of free DHA of TP-312 administered via intravenous injection (TP-312iv) versus TP-312 administered via oral gavage (TP-312po) versus DHA-FFA administered via oral gavage (DHApo). The data indicate that the Cmax of TP-312iv is approximately 6.4 and 19.3 times greater than TP-312po and DHApo, respectively; the AUC over 1 hour of TP-312iv is approximately 4.9 and 14.7 times greater than TP-312po and DHApo, respectively; and the AUC over 4 hours of TP-312iv is approximately 1.6 times and 5.0 times greater than TP-312po and DHApo, respectively.

TABLE 7

Plasma levels of free DHA of TP-312 (iv).

| Min | ug/mL * | | |
|---|---|---|---|
| | TP-312iv | TP-312po | DHApo |
| — | 0.0 | 0.0 | 0.0 |
| 1 | 66.4 | ** | ** |
| 5 | 15.1 | ** | ** |
| 10 | 16.6 | ** | ** |
| 15 | 17.5 | 0.0 | 0.0 |
| 30 | 16.4 | 4.6 | 1.8 |
| 60 | 12.9 | 6.3 | 1.8 |
| 120 | 8.5 | 10.4 | 2.2 |
| 240 | 7.8 | 5.6 | 3.4 |
| Tmax | 1 min | 2 hrs | 4 hrs |
| Cmax (ug/mL) | 66.4 | 10.4 | 3.4 |
| AUC [0-1 hrs (ug*h/mL)] | 16.3 | 3.3 | 1.1 |
| AUC [0-4 hrs (ug*h/mL)] | 43.3 | 27.6 | 8.7 |

* Molar dose equivalent, baseline adjusted
** No blood samples on studies with oral doses Ophthalmic Formulations In an embodiment where the ophthalmic formulation is an aqueous formulation, it has been determined in mice that certain formulations can be administered to the surface of the eye without producing irritation that would make them unsuitable for such application. Irritation parameters of TP-211-1, TP-212-1, TP-311-1 and TP-312-1 related to hyperemia, squinting, and discharge were determined in Balb/C mice. Mice were dosed topically to the cornea using a calibrated micropipette, with a 3 μL drop of treatment in each eye four times daily for 3 consecutive days at various concentrations.

TP-211-1 is Lysyl-lysine EPA. TP-212-1 is Lysyl-lysine bis-EPA. TP-311-1 is Lysyl-lysine DHA. TP-312-1 is Lysyl-lysine bis-DHA. The study drugs were prepared using phosphate buffered saline (PBS) to reach target concentrations ranging from 0.1% to 1.0%.

The animals were monitored for scratching at the eye or any other abnormal behavior post-dose. Ocular exams were conducted on Days 1 and 3 with use of a Micron III camera system to take high resolution videos of the right eye of each animal Clinical signs including but not limited to hyperemia, discharge, lid swelling, and squinting were evaluated by trained personnel who was masked as to group assignment. Each clinical sign was graded on a scale of 0-4, with the exception of lid swelling which was graded on a scale of 0-2. Scores were averaged and are expressed as the mean±SEM for each group. Statistical significance was assessed between the treatment arms and the vehicle group. Any significance is noted by asterisks (*=$p<0.05$, =$p<0.01$, *=$p<0.001$).

Summary of Observations

TP-211-1: TP-211-1 was tested at 0.5%, 0.25%, and 0.1% concentrations. The 0.5% concentration caused some initial increase in hyperemia, which returned to baseline levels by the last dose on Day 3. The other concentrations maintained baseline levels of hyperemia throughout both evaluations. There were no statistically significant changes in squinting for this test article. Therefore, TP-211-1 is not irritating at concentrations of less than 0.5%.

TP-311-1: TP-311-1 was tested at 1.0% and 0.5% concentrations. The 1.0% group had elevated hyperemia after the first dose administration with no increase in squinting levels. The lowest concentration of 0.5% did not cause any increase in hyperemia or squinting throughout. Therefore, TP-311-1-1 is not irritating at concentrations of less than 1.0%.

TP-212-1: TP-212-1 was tested at 1.0% and 0.5% concentrations. The 1.0% and 0.5% concentrations showed an increase in hyperemia (but not squinting) after the first dose. However, this initial increase in hyperemia returned to baseline levels by the final evaluation. This indicates that concentrations of less than 1.0% of TP-212-1 may cause some initial irritation upon the very first installation, but the animals acclimated well to repeat dosing.

TP-312-1: TP-312-1 was tested at 1.0%, 0.5% and 0.1% concentrations. The 1.0% and 0.5% concentrations caused some initial hyperemia after the first dose. The 0.1% concentration did not cause any significant increase in hyperemia after the first dose. All concentrations remained at baseline levels of hyperemia by the last dose of the day, and none of the concentrations caused squinting throughout the study. Therefore, TP-312-1 is well tolerated in mice at a concentration of less than 1.0%.

Summary: All concentrations noted above appeared comfortable by Day 3 of dosing.

FIGS. 5-8 show each endpoint for one of the test compounds, TP-312-1. Comparable data was compiled for the other test articles. In each figure, A is the pre-dose/baseline, B is 30 minutes post dose, and C is the delta of A and B.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A compound of Formula I, or an enantiomer, polymorph, solvate, or hydrate thereof, which is a salt of an amino acid moiety and one or two fatty acids, A and B:

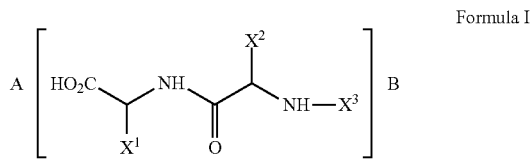

Formula I wherein
A and B are the same or different, and each of A and B is independently selected from the group consisting of eicosapentaenoic acid (EPA), docosahexaenoic acid (DHA), and docosapentaenoic acid (DPA),
either A or B, but not both, may be absent,
$X_1$ and $X_2$ are each independently selected from $(CH_2)_3$—$R_1$, and $(CH_2)_4$—$R_2$, where $R_1$ and $R_2$ are each a basic function which may be the same or different, the basic function being selected from the group consisting of a primary amine, a secondary amine, a tertiary amine, and a guanidine, and
$X_3$ is H.

2. The compound of claim 1, wherein $X_1$ and $X_2$ are both $(CH_2)_4$—$R_2$ and $R_2$ is $NH_3+$.

3. The compound of claim 2, wherein A or B is absent and the remainder is EPA.

4. The compound of claim 2, wherein A and B are both present and are each EPA.

5. The compound of claim 2, wherein A or B is absent and the remainder is DHA.

6. The compound of claim 2, wherein A and B are both present and are each DHA.

7. The compound of claim 2, wherein A or B is absent and the remainder is DPA.

8. The compound of claim 2, wherein A and B are both present and are each DPA.

9. The compound of claim 1, wherein $X_1$ and $X_2$ are both $(CH_2)_3$—$R_1$ and $R_1$ is $NHC(NH_2+)NH_2$.

10. The compound of claim 9, wherein A or B is absent and the remainder is EPA.

11. The compound of claim 9, wherein A and B are both present and are each EPA.

12. The compound of claim 9, wherein A or B is absent and the remainder is DHA.

13. The compound of claim 9, wherein A and B are both present and are each DHA.

14. The compound of claim 9, wherein A or B is absent and the remainder is DPA.

15. The compound of claim 9, wherein A and B are both present and are each DPA.

16. The compound of claim 1, wherein $X_1$ is $(CH_2)_3$—$R_1$, $R_1$ is $NHC(NH_2+)NH_2$, $X_2$ is $(CH_2)_4$—$R_2$ and $R_2$ is $NH_3+$.

17. The compound of claim 16, wherein A or B is absent and the remainder is EPA.

18. The compound of claim 16, wherein A and B are both present and are each EPA.

19. The compound of claim 16, wherein A or B is absent and the remainder is DHA.

20. The compound of claim 16, wherein A and B are both present and are each DHA.

21. The compound of claim 16, wherein A or B is absent and the remainder is DPA.

22. The compound of claim 16, wherein A and B are both present and are each DPA.

23. The compound of claim 1, wherein $X_1$ is $(CH_2)_4$—$R_2$, $R_2$ is $NH_3+$, $X_2$ is $(CH_2)_3$—$R_1$, and $R_1$ is $NHC(NH_2+)NH_2$.

24. The compound of claim 23, wherein A or B is absent and the remainder is EPA.

25. The compound of claim 23, wherein A and B are both present and are each EPA.

26. The compound of claim 23, wherein A or B is absent and the remainder is DHA.

27. The compound of claim 23, wherein A and B are both present and are each DHA.

28. The compound of claim 23, wherein A or B is absent and the remainder is DPA.

29. The compound of claim 23, wherein A and B are both present and are each DPA.

30. A pharmaceutical composition comprising the compound of claim 1, and a carrier.

31. The pharmaceutical composition of claim 30, wherein the composition is a solid oral dosage form.

32. The pharmaceutical composition of claim 30, wherein the composition is an intravenous dosage form.

33. The pharmaceutical composition of claim 30, wherein the composition is an ophthalmic formulation.

34. A package or kit comprising a unit dosage form of the pharmaceutical composition of claim 30, at least one container for holding the unit dosage forms, and instructions for use.

35. The pharmaceutical composition of claim 30, wherein the composition is a parenteral dosage form.

36. A method for treating a metabolic disease or disorder in a subject, the method comprising administering to the subject a pharmaceutical composition comprising the compound of claim 1, wherein the metabolic disease or disorder is selected from the group consisting of hypertriglyceridemia, severe hypertriglyceridemia, hypercholesterolemia, pre-diabetes, fatty liver disease, and obesity.

37. The method of claim 36, wherein the subject is human.

38. A method for treating a cardiovascular disease or disorder in a subject, the method comprising administering to the subject a pharmaceutical composition comprising the compound of claim 1, wherein the cardiovascular disease or disorder is selected from the group consisting of atrial fibrillation, myocardial infarction, and congestive heart failure.

39. The method of claim 38, wherein the subject is human.

40. A method for treating an inflammatory disease or disorder in a subject, the method comprising administering to the subject a pharmaceutical composition comprising the compound of claim 1, wherein the inflammatory disease or disorder is selected from the group consisting of arthritis, irritable bowel syndrome, ophthalmic inflammation disorders, and dry eye syndrome.

41. The method of claim 40, wherein the subject is human.

42. A method for treating a gastrointestinal disorder or complication thereof in a subject, the method comprising administering to the subject a pharmaceutical composition comprising the compound of claim 1, wherein the gastrointestinal disorder or complication thereof is selected from the group consisting of bowel obstruction, short bowel syndrome, Gastroschisis, prolonged diarrhea, high-output fistula, Crohn's disease, ulcerative colitis, colon cancer, familial adenomatous polyposis, parenteral nutrition-associated liver disease, essential fatty acid deficiency, a congenital gastrointestinal anomaly, and necrotizing enterocolitis.

43. The method of claim 42, wherein the gastrointestinal disorder or complication is bowel obstruction.

44. The method of claim 42, wherein the subject is human.

45. A method for treating a neurological disorder in a subject, the method comprising administering to the subject a pharmaceutical composition comprising the compound of claim 1, wherein the neurological disorder is selected from the group consisting of Alzheimer's disease, attention deficit hyperactivity disorder (ADHD), depression, traumatic brain injury, spinal cord injury, ischemic stroke, and concussion.

46. The method of claim 45, wherein the subject is human.

* * * * *